(12) United States Patent
Sharma et al.

(10) Patent No.: US 11,667,621 B2
(45) Date of Patent: Jun. 6, 2023

(54) ANTIESTROGEN COMPOUNDS

(71) Applicants: STEVENS INSTITUTE OF TECHNOLOGY, Hoboken, NJ (US); MEMORIAL SLOAN-KETTERING CANCER CENTER, New York, NY (US); THE BOARD OF TRUSTEES OF THE UNIVERSITY OF ILLINOIS, Urbana, IL (US)

(72) Inventors: Abhishek Sharma, Edison, NJ (US); Sarat Chandarlapaty, New York, NY (US); Lucia Wang, Jersey City, NJ (US); Shengjia Lin, Secaucus, NJ (US); Weiyi Toy, New York, NY (US); John Katzenellenbogen, Urbana, IL (US)

(73) Assignees: STEVENS INSTITUTE OF TECHNOLOGY, Hoboken, NJ (US); THE BOARD OF TRUSTEES OF THE UNIVERSITY OF ILLINOIS, Urbana, IL (US); MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 17/251,771

(22) PCT Filed: Jun. 11, 2019

(86) PCT No.: PCT/US2019/036526
§ 371 (c)(1),
(2) Date: Dec. 11, 2020

(87) PCT Pub. No.: WO2019/241231
PCT Pub. Date: Dec. 19, 2019

(65) Prior Publication Data
US 2021/0130320 A1    May 6, 2021

Related U.S. Application Data

(60) Provisional application No. 62/683,383, filed on Jun. 11, 2018.

(51) Int. Cl.
| | | |
|---|---|---|
| C07D 401/04 | (2006.01) | |
| C07C 233/20 | (2006.01) | |
| C07C 233/21 | (2006.01) | |
| C07D 209/12 | (2006.01) | |
| C07D 333/64 | (2006.01) | |
| C07D 409/14 | (2006.01) | |

(52) U.S. Cl.
CPC ...... C07D 401/04 (2013.01); C07C 233/20 (2013.01); C07C 233/21 (2013.01); C07D 209/12 (2013.01); C07D 333/64 (2013.01); C07D 409/14 (2013.01)

(58) Field of Classification Search
CPC .................. C07D 409/14; C07D 333/64
See application file for complete search history.

(56) References Cited

U.S. PATENT DOCUMENTS 5,672,574 A * 9/1997 Evans ............... C08K 5/005
                                                                524/334

FOREIGN PATENT DOCUMENTS

| WO | 2014108452 A1 | 7/2014 |
| WO | 2017185036 A1 | 10/2017 |
| WO | 2017197056 A1 | 11/2017 |

OTHER PUBLICATIONS

"Breast cancer prevention", http://www.mayoclinic.com/health/breast-cancer-prevention/WO00091, accessed Aug. 28, 2013, online Dec. 12, 2012 (Year: 2012).*
BAI. European Journal of Medicinal Chemistry, 2021, 221, 113543 (Year: 2021).*
PCT International Search Report & Written Opinion for PCT/US2019/036526, dated Nov. 12, 2019, 8 pages.
"Pubchem CID 104772" Create Date: Jun. 24, 2005 (Jun. 24, 2005) Date Accessed: Oct. 8, 2019 (Oct. 8, 2019); p. 2, compound listed.

* cited by examiner

*Primary Examiner* — Noble E Jarrell
(74) *Attorney, Agent, or Firm* — Lewis Roca Rothgerber Christie LLP

(57) ABSTRACT

A genus of proteolysis-targeting chimeras (PROTACs)-type compounds/antiestrogens has now been found that act as selective estrogen receptor degraders (SERDs) and estrogen receptor antagonists by degrading and antagonizing ERa in breast cancer cells. The compounds are of the following genus: The compounds described herein exhibit anti-proliferative effects, and are potentially useful, alone or in combination with other therapies, for the treatment of breast cancer. In general, these compounds combine a tight binding ERa targeting ligand tethered to a recognition motif or degron. Once bound, the degron recruits destructive cellular components and the targeted receptor (i.e., ERa) is degraded (i.e., destroyed) or antagonized.

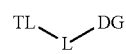

(I)

24 Claims, No Drawings

ANTIESTROGEN COMPOUNDS

CROSS REFERENCE TO RELATED APPLICATION(S)

This application is a national phase of PCT/2019/036526 filed Jun. 11, 2019, which claims priority to and the benefit of U.S. Provisional Patent Application No. 62/683,383 filed Jun. 11, 2018, the entire contents of both of which are incorporated herein by reference.

FIELD OF THE INVENTION

The invention relates to the use of antiestrogens as chemical modulators of estrogen receptor-alpha (ERα) in breast cancer cells. The antiestrogens comprise compounds for the treatment of breast cancer that include scaffolds with ERα-binding ligands tethered to ERα-degradation and/or antagonism-inducing motifs.

BACKGROUND

Estrogen and estrogen receptor-alpha (ERα) are prominent drivers of breast tumorigenesis and breast cancer progression. Therapies for blocking estrogen binding to ERα include selective estrogen receptor modulators (SERMs) and selective estrogen receptor degraders (SERDs). SERMs act as antagonists or mixed agonists/antagonists by modulating receptor conformation thereby regulating coactivator and corepressor recruitment to the receptor. However, many patients eventually relapse with drug-resistant breast cancers after prolonged treatment with SERMs. SERDs, on the other hand, trigger the destruction of ERα upon SERD binding to the receptor and have become the last line of treatment, especially in metastatic breast cancer patients who have become resistant to therapies that inhibit the function of ERα. Unfortunately, the only clinically approved SERD, fulvestrant, exhibits poor oral bioavailability and must be administered via an intramuscular injection, which is dose-limiting and typically painful.

Because they result in the destruction of ERα, SERDs are useful as a stand-alone therapy for breast cancer. In addition, SERDs are useful for restoring cancer cell sensitivity to other therapeutic agents when resistance of cancer cells to said therapeutics involves the increased expression of ERα. For example, resistance to the dual Her2/EGFR antagonist lapatinib is associated with increased expression of ERα. However, sensitivity to lapatinib is restored in these cases upon administration of fulvestrant.

An emerging strategy in the treatment of cancer and other diseases is targeted protein degradation. Molecules that trigger targeted protein degradation bind to the target and subsequently recruit cellular protein degradation machinery to destroy it. Proteolysis-targeting chimeras (PROTACs) refer to therapeutic agents that possess a targeting ligand attached to a recognition motif. The targeting ligand binds to a pocket on the surface of the protein and the recognition motif is recognized by destructive cellular components leading eventually to the protein's destruction. The recognition motif is commonly referred to as a "degron."

The compounds described herein bind to ERα, trigger the destruction of the receptor and/or antagonize the receptor. These compounds are therefore potentially useful in the treatment of breast cancer.

SUMMARY OF THE INVENTION

A genus of proteolysis-targeting chimera (PROTAC)-type compounds has now been found that act as selective estrogen receptor degraders (SERDs) and antagonists. The compounds described herein exhibit anti-proliferative effects, and are potentially useful, alone or in combination with other therapies, for the treatment of breast cancer. In general, these compounds combine a tight binding ERα targeting ligand tethered to a recognition motif or degron. Once bound, the degron recruits destructive cellular components and the targeted receptor (i.e., ERα) is degraded (i.e., destroyed) or antagonized.

In a first aspect the invention relates to compounds of formula (I):

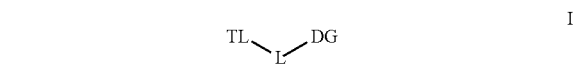

wherein:
TL is chosen from:

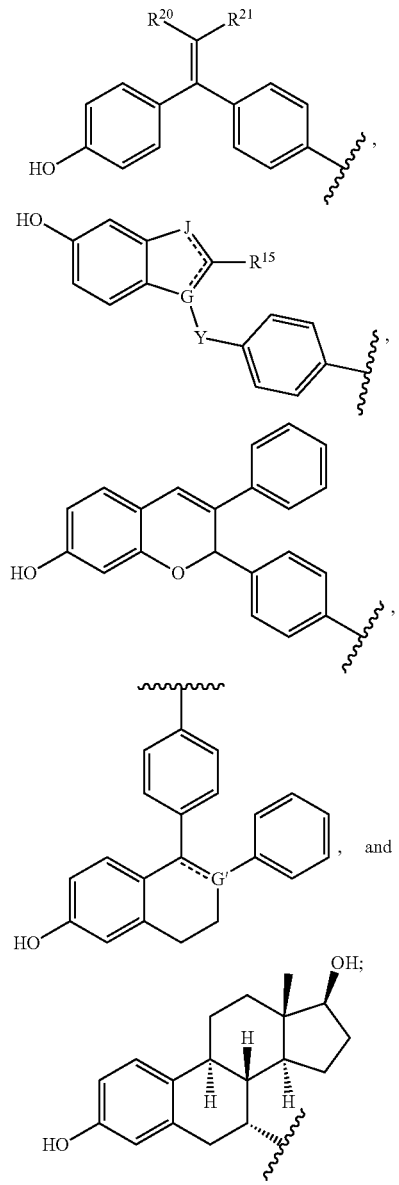

L is selected from divalent $(C_3-C_{10})$hydrocarbyl, $(C_2-C_{10})$oxaalkyl, and $(C_2-C_{10})$azaalkyl;

DG is selected from:

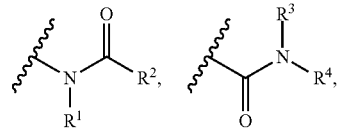

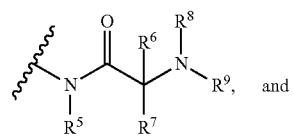

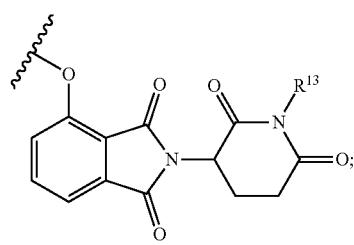

$R^{20}$ and $R^{21}$ are $(C_1-C_{12})$hydrocarbyl, or, taken together along with the carbon to which they are attached, $R^{20}$ and $R^{21}$ form a $(C_3-C_{12})$carbocyclyl;

substructure

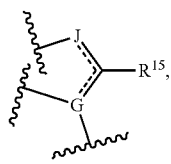

as drawn above, represents either

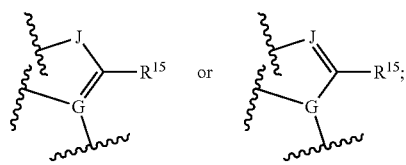

wherein:

J is selected from: S, O, and $NR^{17}$, and, G is C when

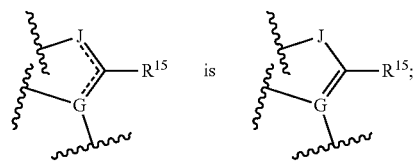

and

J is C—$R^{16}$ and G is N when

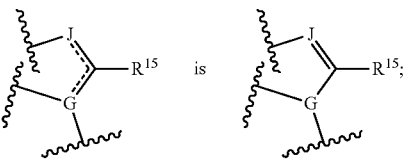

Y is —O— or —$CH_2$—;

===G' represents either a single bond or a double bond connecting a carbon atom to G';

G' is CH or N when ===G' is a single bond, or, G' is C when ===G' is a double bond; ===

$R^1$ and $R^3$ are selected from H and $(C_1-C_3)$alkyl;

$R^2$ is

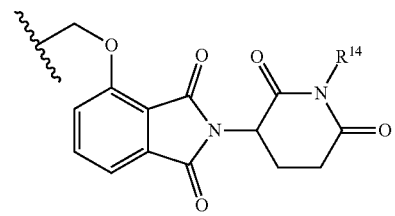

or optionally substituted $(C_1-C_{15})$hydrocarbyl, wherein the optional substituents for $(C_1-C_{15})$hydrocarbyl are selected from halo and $(C_1-C_3)$perfluoroalkyl;

$R^4$ is optionally substituted $(C_1-C_{15})$hydrocarbyl, wherein the optional substituents for $(C_1-C_{15})$hydrocarbyl are selected from halo and $(C_1-C_3)$perfluoroalkyl;

$R^5$ and $R^6$ are selected from H and $(C_1-C_3)$alkyl;

$R^7$ is selected from any of the sidechains present in naturally-occurring α-amino acids;

$R^8$ is H or $(C_1-C_3)$alkyl;

$R^9$ is chosen from H, $(C_1-C_3)$alkyl, or —C(=O)—O—$(C_1-C_6)$alkyl;

$R^{13}$ and $R^{14}$ are selected from H and $(C_1-C_3)$alkyl;

$R^{15}$ is

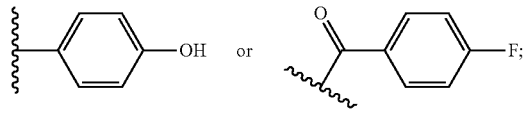 [SMILES: *c1ccc(O)cc1 ; *C(=O)c1ccc(F)cc1]

and

R[16] and R[17] are selected from: H and $(C_1-C_6)$alkyl;

with the proviso that the compound is not:

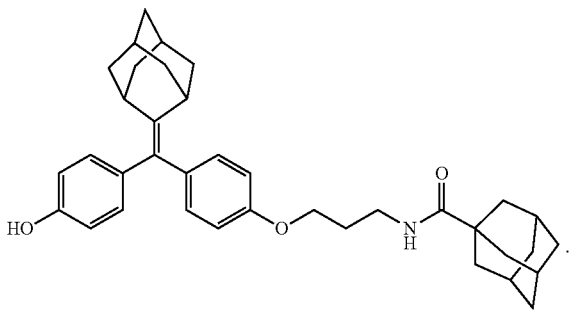 [SMILES: O=C(NCCCOc1ccc(C(=C2C3CC4CC(C3)CC2C4)c2ccc(O)cc2)cc1)C12CC3CC(CC(C3)C1)C2]

In a second aspect, the invention relates to methods and uses of the above-described compounds in medicine, particularly for the treatment of breast cancer. These methods include administering to a patient a therapeutically effective amount of a compound described herein.

In a third aspect, the invention relates to a method for restoring sensitivity to one or more chemotherapeutic agents in the treatment of breast cancer, such as Her2/EGFR antagonists. The method includes administering an effective amount of a compound described herein.

In a fourth aspect, the invention relates to a method for treating breast cancer in a patient, including metastatic breast cancer, where the breast cancer has grown resistant to SERMs. These methods include administering to a patient a therapeutically effective amount of a compound described herein.

In a fifth aspect, the invention relates to a method for destroying ERα receptors by exposing said receptors with a PROTAC compound that includes a targeting ligand (i.e., TL) tethered (i.e., L) to a recognition motif or degron (i.e., DG). These methods include administering to a patient a therapeutically effective amount of a compound described herein.

In a sixth aspect, the invention relates to pharmaceutical compositions comprising the compounds described herein.

DETAILED DESCRIPTION OF THE INVENTION

Substituents are generally defined when introduced and retain that definition throughout the specification and in all independent claims.

In a composition aspect, the invention relates to compounds of formula (I):

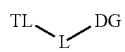

I as described above.

In some embodiments of formula (I), the invention relates to compounds of formula (II):

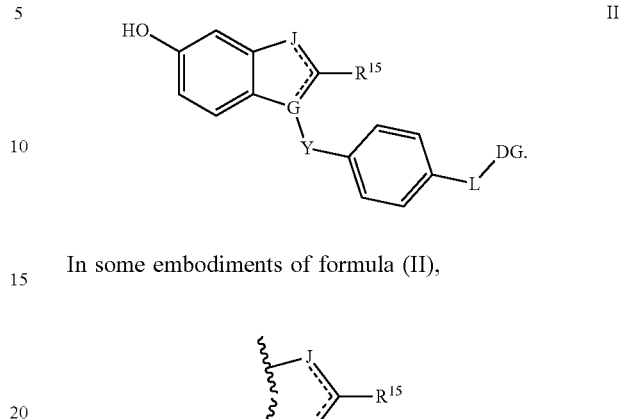

II

In some embodiments of formula (II),

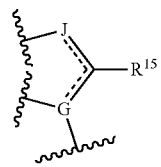

represents the following structure:

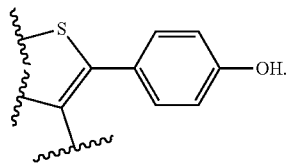 [SMILES: *SC(=C(*)*)c1ccc(O)cc1]

In other embodiments of formula (II),

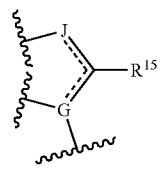

represents the structure:

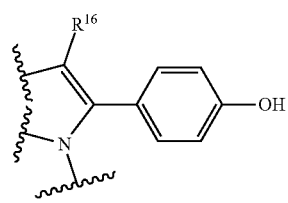

and R[16] is $(C_1-C_3)$alkyl, particularly methyl.

In some embodiments of formula (II), J is S. In other embodiments of formula (II), J is O. In still other embodiments of formula (II), J is C—R[16], wherein R[16] is selected from H and $(C_1-C_6)$alkyl, particularly $(C_1-C_3)$alkyl. In some embodiments of formula (II), J is C—R[16], wherein R[16] is methyl. In other embodiments of formula (II), J is NR[17], wherein R[17] is selected from H and $(C_1-C_3)$alkyl. In some embodiments of formula (II), G is N. In other embodiments of formula (II), G is C. In some embodiments of formula (II), Y is —O—. In other embodiments of formula (II), Y is —CH$_2$—. In some particular embodiments of formula (II), J is S, G is C, and Y is —O—. In other particular embodiments of formula (II), J is C—R$^{16}$, G is N, and Y is —CH$_2$—.

In some embodiments of formula (II), R$^{15}$ is

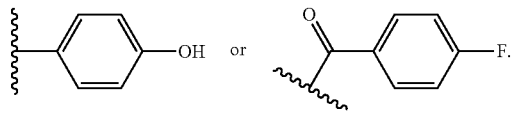

In particular embodiments of formula (II), R$_{15}$ is

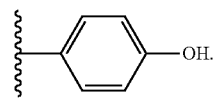

In some embodiments of formula (I), the invention relates to compounds of formula (III):

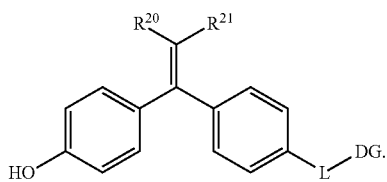

III

In some embodiments of formula (III), R$^{20}$ and R$^{21}$ are independent variants of (C$_1$-C$_{12}$)hydrocarbyl. In some embodiments, taken together along with the carbon to which they are attached, R$^{20}$ and R$^{21}$ form a ring in a (C$_3$-C$_{12}$) carbocyclyl group. As used herein, "carbocyclyl" or "carbocycle" includes monocyclic, bicyclic, and polycyclic rings, including bridged ring structures, e.g., adamantlyl or adamantane, noradamantyl or noradamantane, norbornyl or norbornane, norbornenyl or norbornene, etc.

In some embodiments of formula (I), the invention relates to compounds of formula (IV):

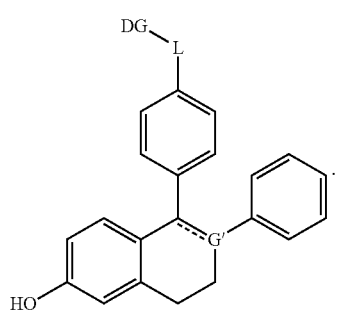

IV

In some embodiments, G' is CH. In other embodiments, G' is N. I yet other embodiments, G' is C. In some embodiments where G' is C, ===G' represents a double bond between a carbon atom and G'. In other embodiments where G' is CH or N, ===G' represents a single bond between a carbon atom and G'.

In some embodiments of formula (I), the invention relates to compounds of formula (V):

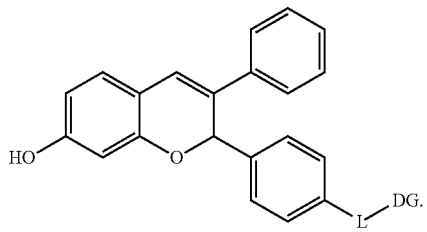

V

In some embodiments of formula (I), the invention relates to compounds of formula (VI):

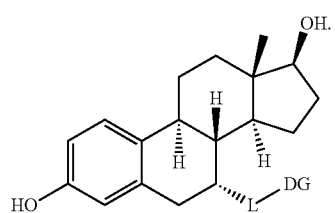

VI

In some embodiments of formulas (I)-(VI), L is divalent (C$_3$-C$_{10}$)hydrocarbyl. In other embodiments of formulas (I)-(VI), L is divalent (C$_2$-C$_{10}$)oxaalkyl. In yet other embodiments of formulas (I)-(VI), L is divalent (C$_2$-C$_{10}$)oxaalkyl. In particular embodiments of formulas (I)-(VI), L is —O(CH$_2$)$_n$— and n is 2, 3, 4, 5, or 6. In some of these embodiments, n is 4.

In some embodiments of formulas (I)-(VI), DG is

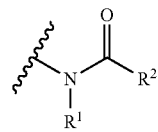

and R$^1$ is chosen from H and (C$_1$-C$_3$)alkyl. In some embodiments of formulas (I)-(VI) where DG is

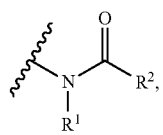

$R^2$ is

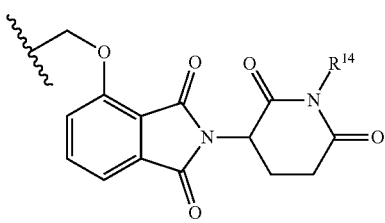

and $R^{14}$ is chosen from H and $(C_1$-$C_3)$alkyl. In some embodiments of formulas (I)-(VI) where DG is

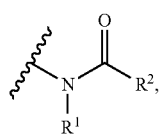

$R^2$ is optionally substituted $(C_1$-$C_{15})$hydrocarbyl, wherein the optional substituents for $(C_1$-$C_{15})$hydrocarbyl are selected from halo and $(C_1$-$C_3)$perfluoroalkyl. In particular embodiments of formulas (I)-(VI) where DG is

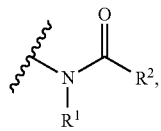

$R^2$ is optionally substituted —$(CH_2)_m R^{22}$, wherein $R^{22}$ is optionally substituted $(C_3$-$C_9)$carbocyclyl and m is chosen from 0, 1, 2, and 3. In these embodiments, the optional substituents for said $(C_3$-$C_9)$carbocyclyl are selected from halo, $(C_1$-$C_3)$alkyl, and $(C_1$-$C_3)$perfluoroalkyl. In particular embodiments of formulas (I)-(VI) where DG is

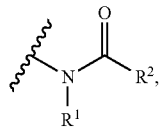

$R^1$ is H.

In some embodiments of formulas (I)-(VI), DG is

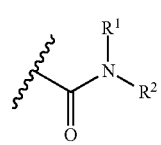

and $R^1$ is chosen from H and $(C_1$-$C_3)$alkyl. In some embodiments of formulas (I)-(VI) where DG is

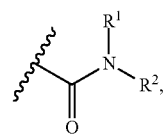

$R^2$ is

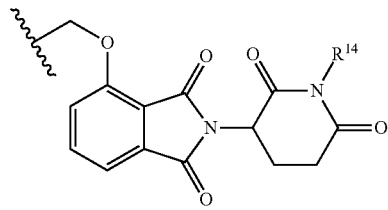

and $R^{14}$ is chosen from H and $(C_1$-$C_3)$alkyl. In some embodiments of formulas (I)-(VI) where DG is

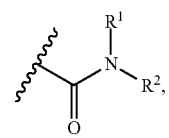

$R^2$ is optionally substituted $(C_1$-$C_{15})$hydrocarbyl, wherein the optional substituents for $(C_1$-$C_{15})$hydrocarbyl are selected from halo and $(C_1$-$C_3)$perfluoroalkyl. In particular embodiments of formulas (I)-(VI) where DG is

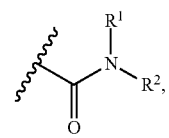

$R^2$ is optionally substituted —$(CH_2)_m R^{22}$, wherein $R^{22}$ is optionally substituted $(C_3$-$C_9)$carbocyclyl and m is chosen from 1, 2, and 3. In these embodiments, the optional substituents for said $(C_3$-$C_9)$carbocyclyl are selected from halo, $(C_1$-$C_3)$alkyl, and $(C_1$-$C_3)$perfluoroalkyl. In particular embodiments of formulas (I)-(VI) where DG is

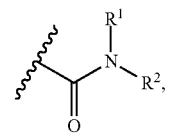

$R^1$ is H.

In some embodiments of formulas (I)-(VI), DG is

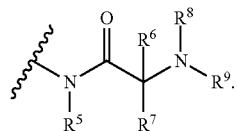

In some of these embodiments, $R^5$, $R^6$ and $R^8$ are selected from H and $(C_1-C_3)$alkyl, particularly H. In these embodiments, $R^7$ is selected from any of the sidechains present in naturally-occurring α-amino acids. By sidechains of naturally-occurring amino acids is meant a naturally occurring amino acid such as alanine, arginine, asparagine, aspartic acid, cysteine, glutamine, glutamic acid, glycine, histidine, isoleucine, leucine, lysine, methionine, phenylalanine, serine, threonine, tryptophan, tyrosine, and valine minus the H₂NCHCOOH residue.

Thus, in exemplary embodiments, $R^7$ is selected from.

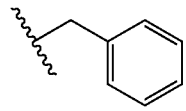 [SMILES: *Cc1ccccc1]

(the sidechain of phenylalanine),

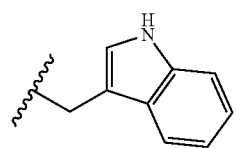 [SMILES: *Cc1c[nH]c2ccccc12]

(the sidechain of tryptophan), and

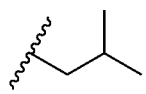 [SMILES: *CC(C)C]

(the sidechain of leucine). In particular embodiments, $R^7$ is

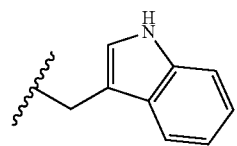

In various embodiments of formulas (I)-(VI) when DG is

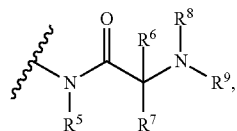

$R^9$ is chosen from H, $(C_1-C_3)$alkyl, or —C(=O)—O—$(C_1-C_6)$alkyl.

In some embodiments of formulas (I)-(VI), DG is

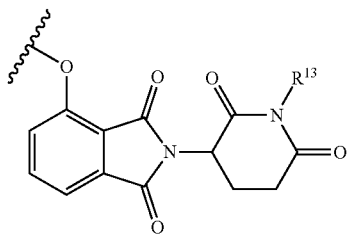

and $R^{13}$ is selected from H and $(C_1-C_3)$alkyl, particularly H.

In summary, the invention relates to:

[1] A compound selected from formulas (I)-(VI).

[2] A compound according to [1] above wherein L is divalent $(C_3-C_{10})$hydrocarbyl.

[3] A compound according to [1] above wherein L is divalent $(C_2-C_{10})$oxaalkyl.

[4] A compound according to [1] above wherein L is divalent $(C_2-C_{10})$azaalkyl.

[5] A compound according to [1] or [2] above wherein L is divalent $(C_3-C_7)$hydrocarbyl.

[6] A compound according to [1] or [3] above wherein L is —O(CH₂)$_n$— and n is 2.

[7] A compound according to [1] or [3] above wherein L is —O(CH₂)$_n$— and n is 3.

[8] A compound according to [1] or [3] above wherein L is —O(CH₂)$_n$— and n is 4.

[9] A compound according to [1] or [3] above wherein L is —O(CH₂)$_n$— and n is 5.

[10] A compound according to [1] or [3] above wherein L is —O(CH₂)$_n$— and n is 6.

[11] A compound according to any one of [1]-[10] above wherein DG is

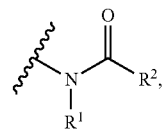

$R^1$ is selected from H and $(C_1-C_3)$alkyl, $R^2$ is —(CH₂)$_m$R²², $R^{22}$ is optionally substituted $(C_3-C_9)$carbocyclyl, wherein the optional substituents for said $(C_3-C_9)$carbocyclyl are selected from halo, $(C_1-C_3)$alkyl, and $(C_1-C_3)$perfluoroalkyl, and m is 0.

[12] A compound according to any one of [1]-[10] above wherein DG is

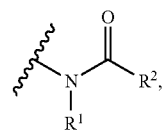

$R^1$ is selected from H and $(C_1-C_3)$alkyl, $R^2$ is —(CH₂)$_m$R²², $R^{22}$ is optionally substituted $(C_3-C_9)$carbocyclyl, wherein the optional substituents for said $(C_3-C_9)$carbocyclyl are selected from halo, $(C_1-C_3)$alkyl, and $(C_1-C_3)$perfluoroalkyl, and m is 1.

[13] A compound according to any one of [1]-[10] above wherein DG is

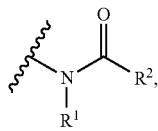

$R^1$ is selected from H and $(C_1$-$C_3)$alkyl, $R^2$ is $—(CH_2)_m R^{22}$, $R^{22}$ is optionally substituted $(C_3$-$C_9)$carbocyclyl, wherein the optional substituents for said $(C_3$-$C_9)$carbocyclyl are selected from halo, $(C_1$-$C_3)$alkyl, and $(C_1$-$C_3)$perfluoroalkyl, and m is 2.

[14] A compound according to any one of [1]-[10] above wherein DG is

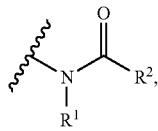

$R^1$ is selected from H and $(C_1$-$C_3)$alkyl, $R^2$ is $—(CH_2)_m R^{22}$, $R^{22}$ is optionally substituted $(C_3$-$C_9)$carbocyclyl, wherein the optional substituents for said $(C_3$-$C_9)$carbocyclyl are selected from halo, $(C_1$-$C_3)$alkyl, and $(C_1$-$C_3)$perfluoroalkyl, and m is 3.

[15] A compound according to any one of [1]-[14] above wherein DG is

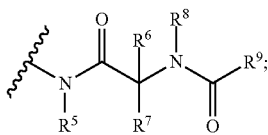

$R^5$, $R^6$ and $R^8$ are selected from H; $R^7$ is selected from any of the sidechains present in naturally-occurring α-amino acids; and $R^9$ is $—O—(C_1$-$C_6)$alkyl.

Where tautomerism is possible for functional groups contained within the compounds described herein, all tautomeric forms are intended to be included.

The compounds described herein may contain one or more asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration.

The symbol "(+/−)" indicates that the enantiomer shown is an arbitrarily chosen representative enantiomer and that the representative enantiomer designated in the shown structure is actually a racemic mixture comprising the shown enantiomer and its mirror image, i.e., antipode. Typically, this symbol indicates that the mixture of enantiomers is approximately a 50/50 ratio as is readily understood by those skilled in the art.

For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R,2R,6S)-rel-" indicates that the three chiral centers are in that relative relationship, which would be depicted in a structural diagram by solid bold and dashed lines, whereas "(1R,2R,6S)" without the "rel" indicates a single enantiomer of that absolute configuration, which would be depicted in a structural diagram by solid and broken wedges.

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genera (I)-(XIV) that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'- dibenzylethylenediamine, chloroprocaine, choline, diethanolamine, ethylenediamine, meglumine (N-methylglucamine) and procaine. Further, pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula (I)-(XIV) to be administered as the raw chemical, it is preferable to present them as a pharmaceutical composition. According to a further aspect, the present invention provides a pharmaceutical composition comprising a compound of formula (I)-(XIV), or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I)-(XIV), or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2$H, $^3$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Compounds that contain isotopes $^{11}$C, $^{13}$N, $^{15}$O and $^{18}$F are well suited for positron emission tomography. Radiolabeled compounds of formula (I)-(XIV) of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating breast cancer in a patient, the method comprising administering to the patient a therapeutically effective amount of a compound of formula (I)-(XIV). In various embodiments, the breast cancer is characterized by the expression of ERα.

The compounds described herein can also be administered in combination with existing methods of treating breast cancer, for example by the administration of SERMs, Her2/EGFR antagonists, aromatase inhibitors, etc. Thus, there is further provided a method of treating breast cancer comprising administering an effective amount of a compound according to formula (I)-(XIV) to a patient, wherein a therapeutically effective amount of one or more additional therapeutic agents are administered to the patient.

Thus, compounds of the present invention are useful in treatment of breast cancer and related diseases, by degrading and antagonizing ERα within breast cancer cells.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, noradamantyl, norbornenyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, adamantyl, noradamantyl, norbornenyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic, bicyclic, and polycyclic hydrocarbon groups of from 3 to 12 carbon atoms. Examples of cycloalkyl groups include cypropyl, cy-butyl, cy-pentyl, norbornyl, adamantyl, noradamantyl, and the like.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane, adamantyl, noradamantyl, norbornenyl, and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy.

Substituents R" are generally defined when introduced and retain that definition throughout the specification and in all independent claims.

Synthesis

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

In general, many compounds of the present disclosure can be prepared by activation of a carboxylic acid and reacting the activated carboxylic acid with an amine-bearing target ligand/tether such as 4-((adamantan-2-ylidene)(4-(4-aminobutoxy)phenyl)methyl)phenol 20, the synthesis of which is shown below:

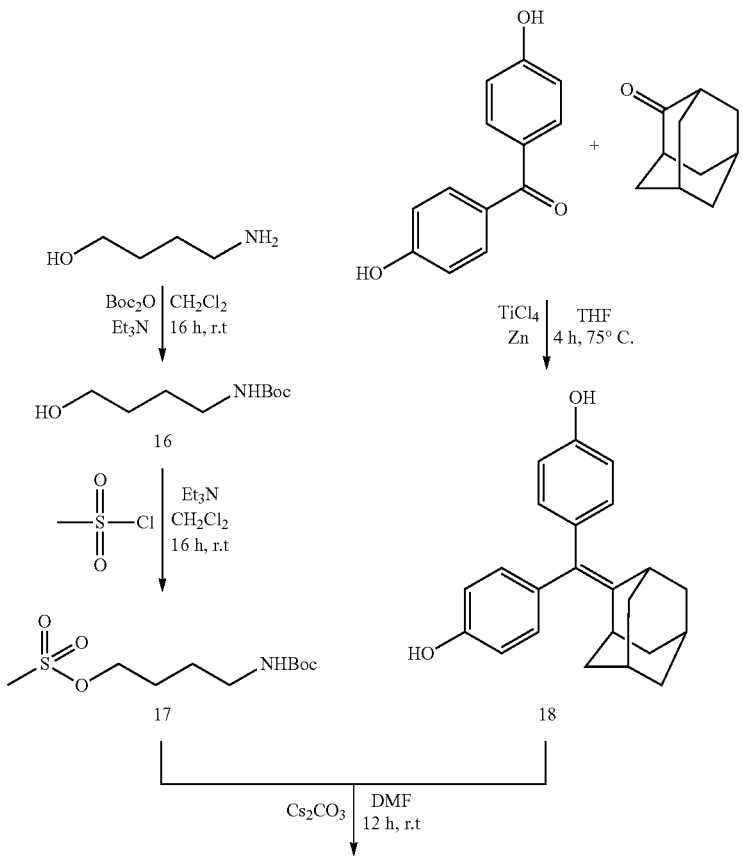

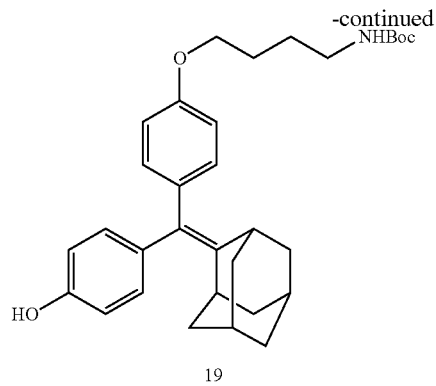
19

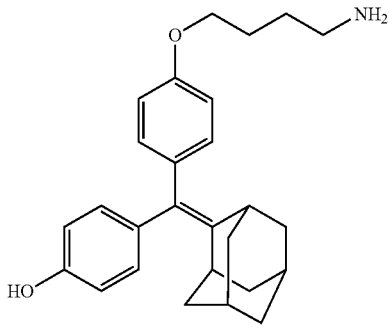
20

The procedures leading to 4-((adamantan-2-ylidene)(4-(4-aminobutoxy)phenyl)-methyl)phenol 20 are detailed below:

4-(Boc-amino)-1-butanol (16). To a solution of Boc$_2$O (2.29 g, 10.49 mmol) in CH$_2$Cl$_2$ (15 mL), 4-amino-butanol (0.74 mL, 8.07 mmol) and triethylamine (3.38 mL, 24.21 mmol) were added dropwise at 0° C. The solution was allowed to warm to rt and stirred overnight. The reaction mixture was quenched by addition of 10% aqueous NH$_4$Cl (25 ml) and extracted with EtOAc (3×100 ml). The combined organic layers were washed with brine (50 ml), dried over Na$_2$SO$_4$, filtered and concentrated to give 16 as a brown oil (1.41 g, quantitative yield). $^1$H NMR (500 MHz, CDCl$_3$): δ 3.65 (t, J=3.2 Hz, 2H), 3.13 (br s, 2H), 1.57 (m, 4H), 1.42 (d, J=1.7 Hz, 9H). $^{13}$C NMR (100 MHz, CDCl$_3$): δ 26.1, 26.6, 28.6, 40.2, 67.6, 79.1, 156.1.

4-((tert-Butoxycarbonyl)amino)butyl methanesulfonate (17). To a solution of 16 (350 mg, 1.85 mmol) in CH$_2$Cl$_2$ (8 mL) was added methane sulfonyl chloride (286 μL, 3.70 mmol) and triethylamine (516 μL, 3.70 mmol) dropwise at 0° C. After the addition, the solution was allowed to warm to rt and stirred overnight. The reaction mixture was quenched by addition of 10% aqueous NH$_4$Cl (10 ml) and extracted with CH$_2$Cl$_2$ (3×80 ml). The combined organic layers were washed with brine (50 ml), dried over Na$_2$SO$_4$, filtered and concentrated to give an orange colored oil which was purified by flash column chromatography (silica gel; EtOAc/hexanes, 0:10 to 8:2) to afford 17 as a brown oil (505 mg, quantitative yield). $^1$H NMR (400 MHz, CDCl$_3$): δ 4.56 (br s, 1H, NH), 4.28-4.19 (m, 2H), 3.15 (br s, 2H), 3.00 (d, J=4.4 Hz, 3H), 1.83-1.73 (m, 2H), 1.65-1.55 (m, 2H), 1.43 (d, J=3.8 Hz, 9H). $^{13}$C NMR (100 MHz, CDCl$_3$): 156.1, 79.4, 69.7, 39.9, 37.5, 28.5, 26.5, 26.4.

4,4'-((Adamantan-2-ylidene)methylene)diphenol (18). Titanium tetrachloride (11.36 mL, 0.10 mol), was added dropwise at −20° C. to a suspension of zinc (13.7 g, 20.95 mol) in THF (140 mL). After removal of the cooling, the reaction mixture was refluxed at 75° C. for 2.5 hours. After allowing the solution to cool down to rt, a mixture of 2-adamantanone (4.2 g, 27.96 mmol) and 4,4-dihydroxybenzophenone (6 g, 28.01 mmol) in THF (40 mL) was added and refluxed again for 4 hours. The heating was stopped and the reaction mixture was cooled, when a 10% K$_2$CO$_3$ solution (200 mL) was poured into the reaction flask and stirred overnight. The resulting emulsion was filtered through celite, extracted with Et$_2$O (3×200 ml), washed with brine (80 ml) and dried (Na$_2$SO$_4$). The solvent was evaporated to afford a white solid, which was further washed with CH$_2$Cl$_2$ to give the pure product (8.8 g, 95% yield) as a white solid. $^1$H NMR (500 MHz, CD$_3$OD): δ 6.94-6.91 (m, 4H), 6.70-6.66 (m, 4H), 2.68 (br s, 2H), 2.12-2.00 (m, 2H), 1.86-1.72 (m, 10H), 1.62-1.54 (m, 2H). $^{13}$C NMR (126 MHz, CD$_3$OD) δ 155.4, 144.6, 134.8, 130.8, 130.3, 114.4, 39.4, 37.1, 34.6, 28.5.

tert-Butyl(4-(4-(adamantan-2-ylidene(4hydroxyphenyl)methyl)phenoxy)butyl)-carbamate (19). A suspension of Cs$_2$CO$_3$ (980 mg, 3.01 mmol) and 18 (500 mg, 1.50 mmol) in DMF (5 mL) was stirred at room temperature for 10 minutes and 17 (241 mg, 0.89 mmol) was added. After stirring for 16 hours at rt, the reaction mixture was quenched with 10% NH$_4$Cl (10 ml) and extracted with EtOAc (3×100 ml). The combined organic layers were washed with brine (50 ml), dried over Na$_2$SO$_4$, filtered and concentrated to give a mixture of unreacted 18, dialkylated side product and the desired monoalkylated product. This mixture was subjected to flash column chromatography (silica gel; EtOAc/hexanes, 0:10 to 8:2) to afford the product as a white solid (195 mg, 26% yield). $^1$H NMR (500 MHz, CDCl$_3$): δ7.04-6.93 (m, 4H), 6.82-6.69 (m, 4H), 4.97 (br s, 1H, OH), 4.62 (br s, 1H, NH), 3.93 (t, J=6.1 Hz, 2H), 3.18 (d, J=6.4 Hz, 2H), 2.78 (br s, 2H), 1.99 (br s, 2H), 1.90-1.74 (m, 12H), 1.69-1.62 (m, 2H), 1.44 (s, 9H). $^{13}$C NMR (100 MHz, CDCl3): δ 157.2, 153.9, 145.9, 136.0, 135.9, 130.9, 130.7, 129.7, 114.9, 113.9, 67.5, 40.5, 39.7, 37.3, 34.6, 28.6, 28.4, 27.0, 26.8. HRMS-ESI: m/z [M+Na]$^+$ for C$_{32}$H$_{41}$NO$_4$Na, calculated 526.2933; observed 526.2957.

4-(Adamantan-2-ylidene(4-(4-aminobutoxy)phenyl)methyl)phenol (20). To a solution of 19 (195 mg, 0.39 mmol) in CH$_2$Cl$_2$ (6 mL) trifluoroacetic acid (TFA, 6 mL) was added. After stirring at room temperature for 16 hours, TFA was removed by passing a stream of compressed air and co-evaporation with acetonitrile. The concentrated residue was subjected to flash column chromatography (silica gel; MeOH/CH$_2$Cl$_2$, 0:10 to 2:8) to afford 20 as a brown oil (253 mg, quantitative yield). $^1$H NMR (400 MHz, CD$_3$OD): δ 7.00 (d, J=8.7 Hz, 2H), 6.89 (d, J=8.6 Hz, 2H), 6.82 (d, J=8.7 Hz, 2H), 6.68 (d, J=8.6 Hz, 2H), 4.06-3.98 (m, 2H), 3.01 (t, J=7.3 Hz, 2H), 2.75 (d, J=14.2 Hz, 2H), 1.98 (br s, 2H), 1.88 (br s, 14H). $^{13}$C NMR (126 MHz, CD$_3$OD) δ 158.4, 156.6, 146.1, 137.2, 135.7, 131.6, 131.5, 115.6, 114.8, 68.1, 40.5, 38.2, 35.7, 35.6, 35.4, 30.1, 29.6, 27.2, 25.6. HRMS-ESI: m/z [M+H]$^+$ for C$_{27}$H$_{34}$NO$_2$, calculated 404.2585; observed 404.2585.

4-(Adamantan-2-ylidene(4-(4-aminobutoxy)phenyl)methyl)phenol 20 represents a first example of an amine-bearing target ligand/tether that may be reacted with various activated carboxylates to form a recognition motif (i.e., degron). By analogy, 4-((adamantan-2-ylidene)(4-(2-aminoethoxy)phenyl)-methyl)phenol 21, 4-((adamantan-2-ylidene)(4-(2-aminopropoxy)phenyl)methyl)phenol 22, and 4-((adamantan-2-ylidene)(4-((6-aminohexyl)oxy)phenyl)methyl)phenol 23 may be formed from a similar set of procedures starting with aminoethanol, 3-aminopropan-1-ol, and 6-aminohexan-1-ol respectively:

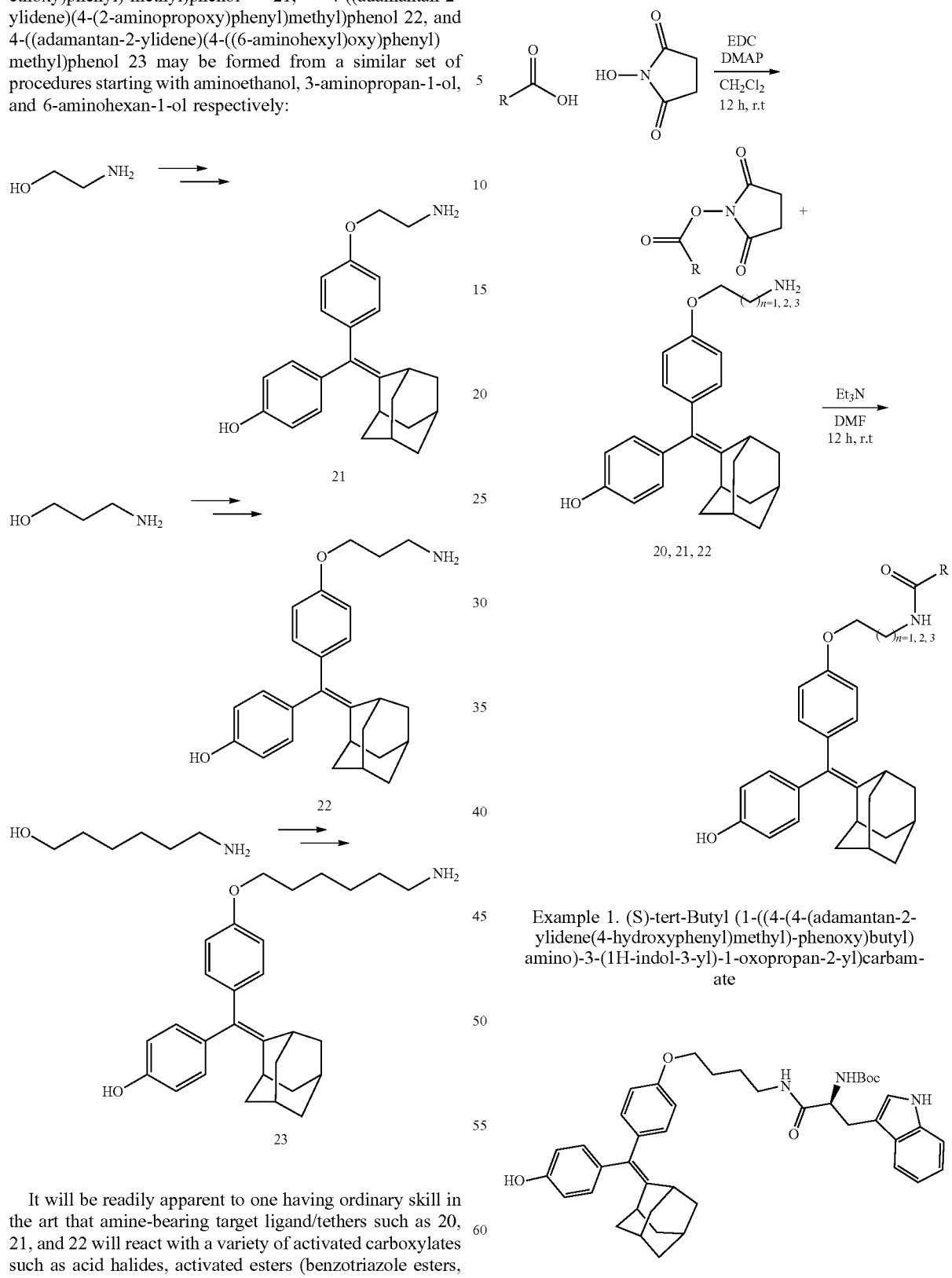

It will be readily apparent to one having ordinary skill in the art that amine-bearing target ligand/tethers such as 20, 21, and 22 will react with a variety of activated carboxylates such as acid halides, activated esters (benzotriazole esters, succinimide esters, etc.), anhydrides (both symmetric and asymmetric), etc. The following shows examples using succinimide esters and amine-bearing target ligand/tethers 20, 21, and 22 to form compounds of formula I and III according to the general scheme shown below:

Example 1. (S)-tert-Butyl (1-((4-(4-(adamantan-2-ylidene(4-hydroxyphenyl)methyl)-phenoxy)butyl)amino)-3-(1H-indol-3-yl)-1-oxopropan-2-yl)carbamate Example 1

A solution of N-Boc-L-tryptophan (100 mg, 0.33 mmol) and N-hydroxysuccinimide (42 mg, 0.36 mmol) in CH$_2$Cl$_2$ (2 mL) was stirred for 15 minutes at 0° C. EDC HCl (69 mg, 0.36 mmol) and 4-dimethylaminopyridine (6 mg, 0.05 mmol) were dissolved in CH$_2$Cl$_2$ (2 mL) and added dropwise to the reaction mixture, which was stirred for 12 h at room temperature. The reaction mixture was diluted with dichloromethane (15 ml), washed with brine (5 ml), dried over Na$_2$SO$_4$ and concentrated to afford the NHS ester which was used as such in the next step.

To a stirred solution of adamantane amine 20 (38 mg, 0.09 mmol) in DMF (1 mL) at 0° C., a solution of above NHS ester (39.9 mg, 0.10 mmol) in DMF (1 mL) was added. This reaction mixture was allowed to warm to room temperature and stirred for 12 h. Thereafter, the reaction mixture was concentrated, diluted with ethyl acetate (15 mL), washed with brine (5 ml) and dried over Na$_2$SO$_4$. The organic layer was concentrated and the obtained residue was subjected to flash column chromatography (silica gel; EtOAc/hexanes, 0:10 to 8:2) to afford the product (33 mg, 26% yield). $^1$H NMR (400 MHz, CDCl$_3$): δ 8.04 (br s, 1H), 7.62 (d, J=7.8 Hz, 1H), 7.29-7.24 (m, 2H), 7.14 (t, J=7.5 Hz, 1H), 7.07 (t, J=7.4 Hz, 1H), 7.02-6.92 (m, 5H), 6.76-6.68 (m, 4H), 5.89 (br s, 1H, OH), 5.29 (br s, 1H, NH), 4.40 (br s, 1H, NH), 3.74 (t, J=5.2 Hz, 2H), 3.27 (dd, J=5.1, 14.4 Hz, 1H), 3.18-3.03 (m, 3H), 2.80 (br s, 2H), 1.99 (br s, 2H), 1.85 (br s, 10H), 1.42 (s, 13H). $^{13}$C NMR (100 MHz, CDCl$_3$): δ 172.0, 157.1, 154.4, 145.8, 136.3, 136.1, 135.6, 130.8, 130.7, 129.7, 127.4, 123.4, 122.4, 119.9, 119.0, 115.0, 113.9, 111.4, 67.3, 55.6, 39.7, 39.2, 37.3, 34.6, 28.8, 28.45, 28.36, 26.4, 26.0. HRMS-ESI: m/z [M+H]$^+$ for C$_{43}$H$_{52}$N$_3$O$_5$, calculated 690.3902; observed 690.3898.

Examples 2-14 were synthesized using analogous procedures as described in example 1:

Example 2. (S)-tert-Butyl (1-((4-(4-(adamantan-2-ylidene(4-hydroxyphenyl)methyl)-phenoxy)butyl)amino)-4-methyl-1-oxopentan-2-yl)carbamate

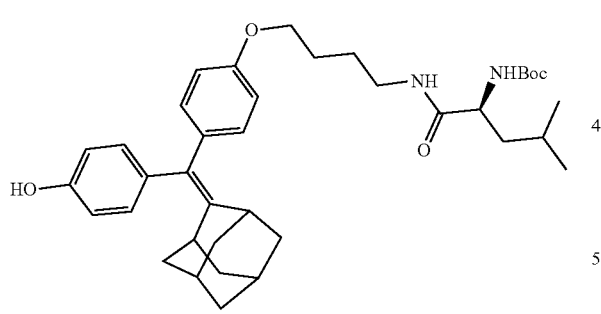

Example 2

Colorless oil: $^1$H NMR (500 MHz, CDCl$_3$): δ 7.02-6.91 (m, 4H), 6.78-6.71 (m, 4H), 6.53 (br s, 1H, OH), 5.03 (br s, 1H, NH), 4.07 (br s, 1H, NH), 3.88 (t, J=5.6 Hz, 2H), 3.28 (q, J=5.9, 6.6 Hz, 2H), 2.78 (d, J=13.6 Hz, 2H), 1.98 (br s, 2H), 1.85 (br s, 10H), 1.77-1.70 (m, 2H), 1.68-1.57 (m, 5H), 1.42 (s, 9H), 0.90 (t, J=5.7 Hz, 6H). 13C NMR (126 MHz, CDCl3): δ 172.9, 157.1, 156.1, 154.5, 145.6, 136.0, 135.4, 130.8, 130.7, 129.8, 115.0, 113.8, 80.4, 67.2, 53.2, 41.3, 39.7, 39.3, 39.1, 37.3, 34.53, 34.50, 29.8, 28.4, 28.3, 26.7, 26.3, 24.9, 23.0, 22.2. HRMS-ESI: m/z [M+H]$^+$ for C$_{38}$H$_{53}$N$_2$O$_5$, calculated 617.3949; observed 617.3947.

Example 3. (S)-tert-Butyl(1-((4-(4-(adamantan-2-ylidene(4-hydroxyphenyl)methyl)-phenoxy)butyl)amino)-1-oxo-3-phenylpropan-2-yl)carbamate

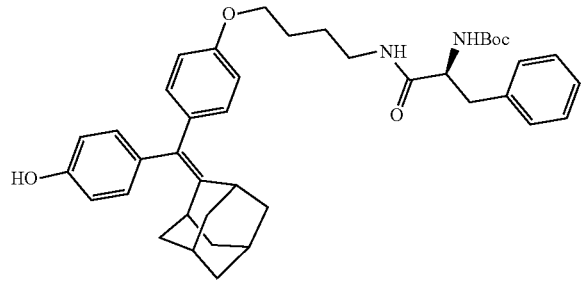 [SMILES: CC(C)(C)OC(=O)N[C@@H](Cc1ccccc1)C(=O)NCCCCOc1ccc(C(=C2C3CC4CC(C3)CC2C4)c2ccc(O)cc2)cc1]

Example 3

Colorless oil. $^1$H NMR (500 MHz, CDCl$_3$): δ 7.31-7.24 (m, 2H), 7.26-7.17 (m, 3H), 7.00 (dd, J=8.5, 19.0 Hz, 4H), 6.80-6.73 (m, 4H), 6.53 (br s, 1H, OH), 5.98 (br s, 1H, NH), 5.20 (br s, 1H, NH), 4.34-4.26 (m, 1H), 3.86-3.84 (m, 2H), 3.29-3.15 (m, 2H), 3.08-3.01 (m, 2H), 2.81 (d, J=11.2 Hz, 2H), 2.00 (br s, 2H), 1.86 (br s, 10H), 1.61 (br s, 2H), 1.52 (br s, 2H), 1.42 (s, 9H). $^{13}$C NMR (126 MHz, CDCl$_3$): δ 171.4, 157.1, 154.4, 145.7, 136.8, 136.0, 135.6, 130.8, 130.7, 129.7, 129.4, 128.8, 127.1, 114.9, 113.9, 109.9, 80.5, 67.2, 56.3, 39.7, 39.2, 38.9, 37.3, 34.54, 34.51, 29.8, 28.4, 28.3, 26.5, 26.2. HRMS-ESI: m/z [M+H]$^+$ for C$_{41}$H$_{51}$N$_2$O$_5$, calculated 651.3793; observed 651.3789.

Example 4. N-(2-(4-(Adamantan-2-ylidene(4-hydroxyphenyl)methyl)phenoxy)ethyl)-adamantane-1-carboxamide

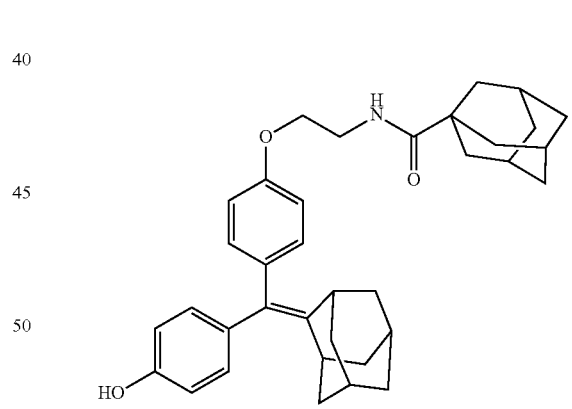

Example 4

Colorless oil. $^1$H NMR (500 MHz, DMSO-d$_6$): δ 9.26 (s, 1H), 7.53 (t, J=5.7 Hz, 1H), 6.92 (d, J=8.6 Hz, 2H), 6.86-6.78 (m, 4H), 6.64 (d, J=8.3 Hz, 2H), 3.92 (t, J=6.0 Hz, 2H), 3.35 (q, J=5.9 Hz, 2H), 2.68 (s, 1H), 2.65 (br s, 1H), 1.97-1.88 (m, 5H), 1.75 (d, J=26.1 Hz, 16H), 1.62 (q, J=12.3 Hz, 6H). $^{13}$C NMR (126 MHz, DMSO-d$_6$): δ 177.2, 156.7, 155.6, 144.2, 135.3, 133.3, 130.1, 130.0, 129.6, 114.7, 114.0, 65.9, 38.7, 38.3, 36.6, 36.1, 33.83, 33.78, 27.6, 27.5. HRMS-ESI: m/z [M+H]$^+$ for C$_{36}$H$_{44}$NO$_3$, calculated 538.3321; observed 538.3326.

Example 5. N-(3-(4-(Adamantan-2-ylidene(4-hydroxyphenyl)methyl)phenoxy)propyl)-adamantane-1-carboxamide

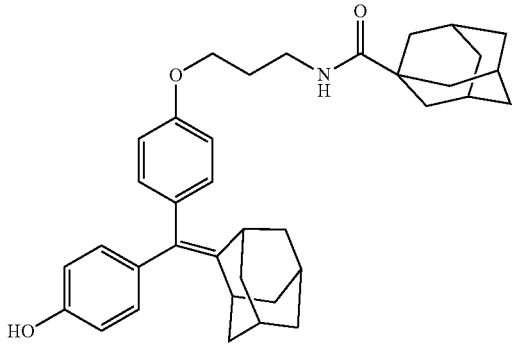 [SMILES: O=C(NCCCOc1ccc(C(=C2C3CC4CC(C3)CC2C4)c2ccc(O)cc2)cc1)C12CC3CC(CC(C3)C1)C2]

Example 5

Colorless oil. $^1$H NMR (500 MHz, CDCl$_3$): δ 7.06-7.01 (m, 2H), 6.98-6.92 (m, 2H), 6.80-6.74 (m, 4H), 6.29 (br s, 1H, NH), 4.02 (t, J=5.4 Hz, 2H), 3.45 (q, J=5.3 Hz, 2H), 2.78 (d, J=22.6 Hz, 2H), 2.05-1.94 (m, 7H), 1.84 (br s, 16H), 1.70 (q, J=12.2 Hz, 6H). $^{13}$C NMR (126 MHz, CDCl$_3$): δ 178.6, 156.7, 154.6, 145.9, 136.5, 135.3, 130.8, 130.8, 129.7, 115.0, 113.7, 67.1, 40.7, 39.75, 39.72, 39.3, 38.2, 37.3, 36.6, 34.6, 34.5, 28.8, 28.3, 28.2. HRMS-ESI: m/z [M+H]$^+$ for C$_{37}$H$_{46}$NO$_3$, calculated 552.3473; observed 552.3473.

Example 6. N-(4-(4-(Adamantan-2-ylidene(4-hydroxyphenyl)methyl)phenoxy)-butyl)adamantane-1-carboxamide

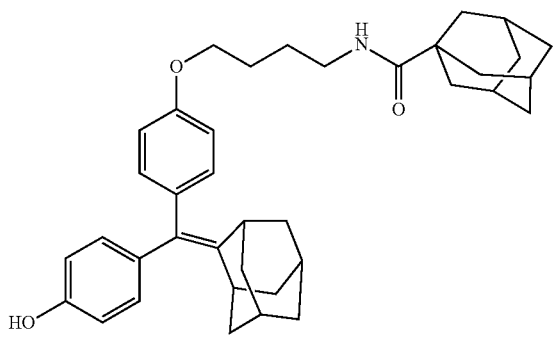 [SMILES: O=C(NCCCCOc1ccc(C(=C2C3CC4CC(C3)CC2C4)c2ccc(O)cc2)cc1)C12CC3CC(CC(C3)C1)C2]

Example 6

Brown oil. $^1$H NMR (500 MHz, CDCl$_3$): δ 7.05-6.92 (m, 4H), 6.80-6.73 (m, 4H), 6.29 (br s, 1H, OH), 5.83 (t, J=5.5 Hz, 1H, NH), 3.92 (t, J=6.0 Hz, 2H), 3.31 (q, J=6.8 Hz, 2H), 2.78 (d, J=17.5 Hz, 2H), 1.99 (d, J=12.2 Hz, 5H), 1.83 (br s, 16H), 1.78-1.73 (m, 2H), 1.73-1.62 (m, 8H). $^{13}$C NMR (126 MHz, CDCl$_3$): δ 178.6, 157.1, 154.6, 145.7, 136.1, 135.4, 130.8, 129.8, 115.0, 113.8, 67.3, 40.7, 39.7, 39.7, 39.4, 39.1, 37.3, 37.3, 36.6, 36.6, 34.6, 34.5, 28.4, 28.2, 26.8, 26.5. HRMS-ESI: m/z [M+H]$^+$ for C$_{38}$H$_{48}$NO$_3$, calculated 566.3629; observed 566.3633.

Example 7. N-(4-(4-(Adamantan-2-ylidene(4-hydroxyphenyl)methyl)phenoxy)butyl)-3,5-dimethyl-adamantane-1-carboxamide

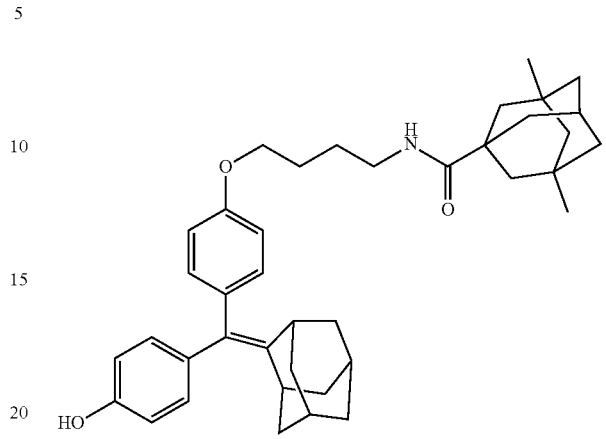

Example 7

White solid (mp=114-119° C.). $^1$H NMR (400 MHz, CDCl$_3$): δ 7.05-6.94 (m, 4H), 6.81-6.72 (m, 4H), 5.95 (br s, 1H, OH), 5.81 (t, J=5.9 Hz, 1H, NH), 3.93 (t, J=5.9 Hz, 2H), 3.31 (q, J=6.6 Hz, 2H), 2.79 (br s, 2H), 2.13-2.07 (m, 1H), 1.99 (br s, 2H), 1.90-1.73 (m, 12H), 1.72-1.64 (m, 4H), 1.51-1.39 (m, 4H), 1.33 (br s, 4H), 1.19-1.07 (m, 2H), 0.82 (s, 6H). $^{13}$C NMR (100 MHz, CDCl$_3$): δ 178.2, 157.1, 154.4, 145.8, 136.1, 135.6, 130.82, 130.76, 115.0, 113.9, 67.4, 50.8, 45.6, 42.9, 42.7, 39.8, 39.2, 38.1, 37.4, 34.6, 31.2, 30.6, 29.4, 28.4, 26.9, 26.5. HRMS-ESI: m/z [M+H]$^+$ for C$_{40}$H$_{52}$NO$_3$, calculated 594.3942; observed 594.3945.

Example 8. N-(4-(4-((Adamantan-2-ylidene)(4-hydroxyphenyl)methyl)phenoxy)butyl)-hexahydro-2,5-methanopentalene-3a(1H)-carboxamide

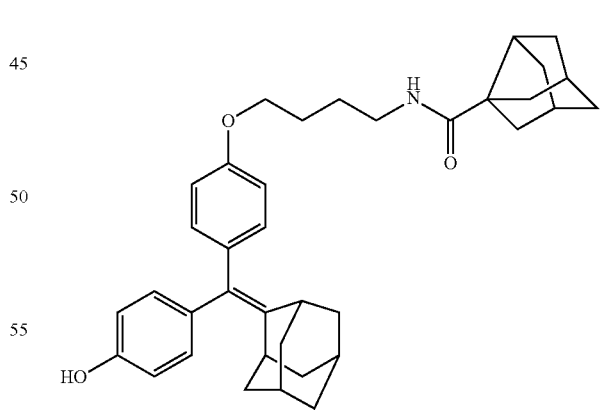

Example 8

Brown oil. $^1$H NMR (400 MHz, CDCl$_3$): δ 7.05-6.92 (m, 4H), 6.81-6.71 (m, 4H), 6.25 (br s, 1H, OH), 5.67 (br s, 1H, NH), 3.95 (t, J=6.2 Hz, 2H), 3.35 (q, J=6.9 Hz, 2H), 2.78 (br s, 2H), 2.64 (t, J=6.6 Hz, 1H), 2.29 (br s, 2H), 2.02-1.93 (m, 4H), 1.89-1.69 (m, 18H), 1.66-1.52 (m, 4H). $^{13}$C NMR (100

MHz, CDCl$_3$): δ 177.9, 157.1, 154.2, 145.9, 136.0, 135.8, 130.9, 130.7, 129.7, 114.9, 113.9, 67.4, 55.2, 47.7, 44.0, 43.6, 39.8, 39.3, 37.8, 37.4, 34.8, 34.6, 28.4, 26.8, 26.7. HRMS-ESI: m/z [M+H]$^+$ for C$_{37}$H$_{46}$NO$_3$, calculated 552.3473; observed 552.3472.

Example 9. (1R, 2S, 4R)—N-(4-(4-(Adamantan-2-ylidene(4-hydroxyphenyl)methyl)phenoxy)-butyl)bicyclo[2.2.1]hept-5-ene-2-carboxamide

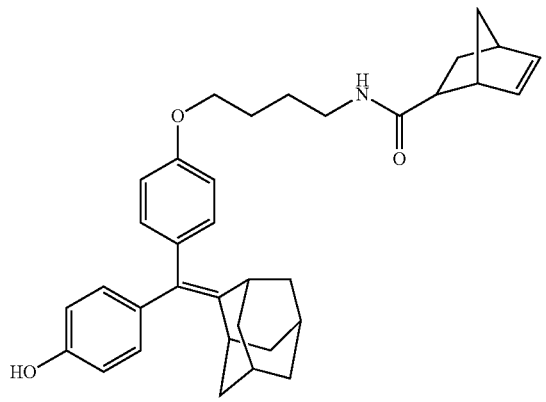 [SMILES: O=C(NCCCCOc1ccc(C(=C2C3CC4CC(C3)CC2C4)c2ccc(O)cc2)cc1)C1CC2C=CC1C2]

Example 9

White solid (mp=79-84° C.). $^1$H NMR (400 MHz, CDCl$_3$): δ 7.03-6.95 (m, 4H), 6.80-6.71 (m, 4H), 6.57 (br s, 1H, OH), 6.15-6.11 (m, 1H), 5.78 (br s, 1H, NH), 3.93 (t, J=5.9 Hz, 2H), 3.33 (q, J=6.2 Hz, 2H), 2.90 (br s, 2H), 2.78 (br s, 2H), 2.03-1.94 (m, 3H), 1.92-1.74 (m, 12H), 1.72-1.62 (m, 3H), 1.37-1.23 (m, 3H). $^{13}$C NMR (100 MHz, CDCl$_3$) δ 176.1, 157.1, 154.4, 145.8, 138.3, 136.1, 135.5, 130.8, 130.7, 129.7, 114.9, 113.9, 67.4, 47.3, 46.5, 45.0, 41.7, 39.7, 39.5, 37.3, 34.6, 34.5, 30.7, 29.8, 28.4, 26.8, 26.6. HRMS-ESI: m/z [M+H]$^+$ for C$_{35}$H$_{42}$NO$_3$, calculated 524.3160; observed 524.3163.

Example 10. N-(4-(4-(Adamantan-2-ylidene(4-hydroxyphenyl)methyl)phenoxy)butyl)-cyclobutanecarboxamide

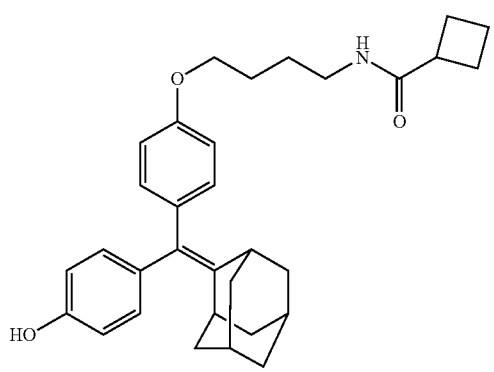 [SMILES: O=C(NCCCCOc1ccc(C(=C2C3CC4CC(C3)CC2C4)c2ccc(O)cc2)cc1)C1CCC1]

Example 10

White foam (mp=88-92° C.). $^1$H NMR (400 MHz, CDCl$_3$) δ 7.03-6.96 (m, 4H), 6.80-6.71 (m, 4H), 5.43 (br s, 1H, NH), 3.95 (t, J=5.9 Hz, 2H), 3.32 (q, J=6.6 Hz, 2H), 3.01-2.88 (m, 1H), 2.78 (br s, 2H), 2.31-2.20 (m, 2H), 2.17-2.07 (m, 3H), 2.02-1.91 (m, 3H), 1.91-1.75 (m, 12H), 1.72-1.64 (m, 2H). $^{13}$C NMR (100 MHz, CDCl$_3$): δ 175.7, 157.0, 154.7, 145.6, 136.2, 135.2, 130.7, 129.8, 115.0, 113.8, 67.3, 40.0, 39.7, 39.3, 37.3, 34.55, 34.49, 28.3, 26.7, 26.5, 25.5, 18.2. HRMS-ESI: m/z [M+H]$^+$ for C$_{32}$H$_{40}$NO$_3$, calculated 486.3003; observed 486.3007.

Example 11. N-(4-(4-(Adamantan-2-ylidene(4-hydroxyphenyl)methyl)phenoxy)butyl)-cyclohexanecarboxamide

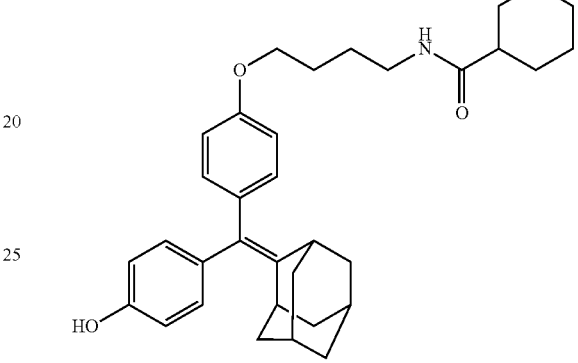

Example 11

Yellow oil. $^1$H NMR (500 MHz, CDCl$_3$): δ 7.04-6.91 (m, 4H), 6.80-6.72 (m, 4H), 5.87 (t, J=5.2 Hz, 1H, NH), 3.92 (t, J=6.0 Hz, 2H), 3.31 (q, J=6.8 Hz, 2H), 2.78 (d, J=15.3 Hz, 2H), 2.10-2.06 (m, 1H), 1.98 (br s, 2H), 1.83 (br s, 12H), 1.79-1.71 (m, 4H), 1.71-1.61 (m, 3H), 1.47-1.33 (m, 2H), 1.29-1.13 (m, 3H). $^{13}$C NMR (126 MHz, CDCl$_3$): δ 13C NMR (126 MHz, CDCl$_3$) δ 176.8, 157.0, 154.6, 145.7, 136.1, 135.4, 130.8, 129.8, 115.0, 113.8, 67.4, 45.8, 39.7, 39.2, 37.3, 34.6, 34.5, 29.8, 28.3, 26.8, 26.5, 25.8. HRMS-ESI: m/z [M+H]$^+$ for C$_{34}$H$_{44}$NO$_3$, calculated 514.3329; observed 514.3321.

Example 12. N-(4-(4-(Adamantan-2-ylidene(4-hydroxyphenyl)methyl)phenoxy)butyl)-cycloheptanecarboxamide

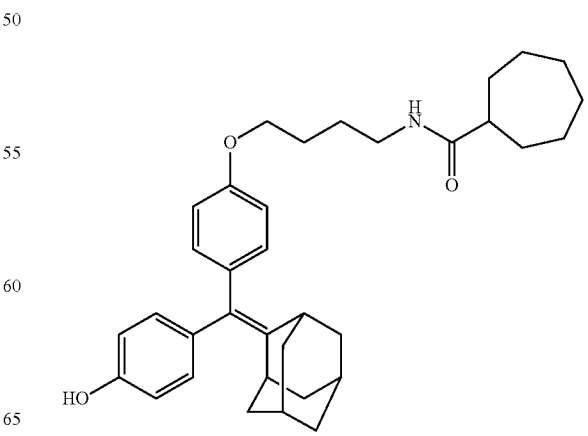

Example 12

Colorless oil. $^1$H NMR (400 MHz, CDCl$_3$): δ 7.05-6.93 (m, 4H), 6.81-6.71 (m, 4H), 5.62 (br s, 1H, NH), 3.92 (t, J=5.9 Hz, 2H), 3.30 (q, J=6.8 Hz, 2H), 2.78 (d, J=13.5 Hz, 2H), 2.23-2.15 (m, 1H), 1.98 (br s, 2H), 1.90-1.79 (m, 12H), 1.79-1.60 (m, 8H), 1.59-1.46 (m, 4H), 1.46-1.34 (m, 2H). $^{13}$C NMR (100 MHz, CDCl$_3$): δ 178.0, 157.0, 154.6, 145.7, 136.1, 135.4, 130.8, 130.7, 129.8, 115.0, 113.9, 67.4, 47.8, 39.7, 39.3, 37.3, 34.6, 34.5, 31.9, 28.4, 28.1, 26.8, 26.6. HRMS-ESI: m/z [M+H]$^+$ for C$_{35}$H$_{46}$NO$_3$, calculated 528.3473; observed 528.3480.

Example 13. N-(4-(4-(Adamantan-2-ylidene(4-hydroxyphenyl)methyl)phenoxy)butyl)-4,4-difluorocyclohexanecarboxamide

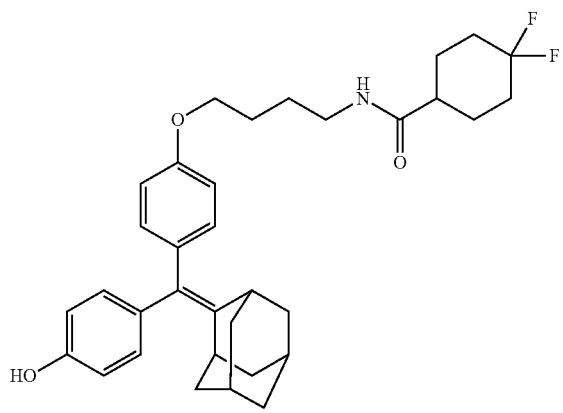 [SMILES: O=C(NCCCCOc1ccc(C(=C2C3CC4CC(C3)CC2C4)c2ccc(O)cc2)cc1)C1CCC(F)(F)CC1]

Example 13

Colorless oil. $^1$H NMR (400 MHz, CDCl$_3$): δ 7.05-6.92 (m, 4H), 6.82-6.69 (m, 4H), 5.68 (br s, 1H, NH), 3.95 (t, J=5.9 Hz, 2H), 3.33 (q, J=6.5 Hz, 2H), 2.77 (br s, 2H), 2.20-2.08 (m, 3H), 1.99 (br s, 2H), 1.94-1.61 (m, 20H). $^{13}$C NMR (100 MHz, CDCl$_3$): δ 174.7, 156.9, 154.5, 145.9, 136.2, 135.4, 130.8, 129.7, 125.31-120.07 (m), 115.0, 113.9, 67.4, 43.1, 39.7, 39.4, 37.3, 34.6, 34.5, 32.95 (t, J$_{C-F}$=24.6 Hz), 28.3, 26.8, 26.5, 26.1, 26.0. HRMS-ESI m/z [M+H]$^+$ for C$_{34}$H$_{42}$F$_2$NO$_3$, calculated 550.3128; observed 550.3136.

Example 14. (trans)-N-(4-(4-(Adamantan-2-ylidene(4-hydroxyphenyl)methyl)phenoxy)-butyl)-4-(trifluoromethyl)cyclohexanecarboxamide

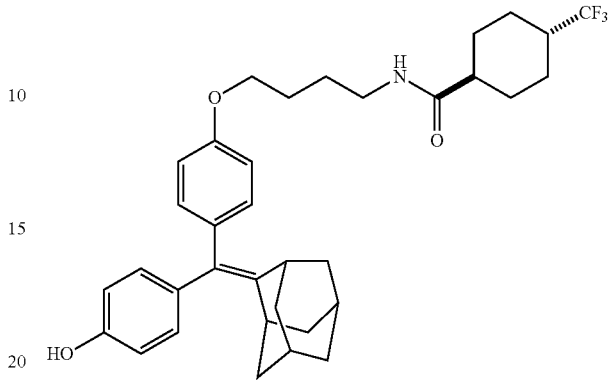

Example 14

Yellow oil. $^1$H NMR (400 MHz, CDCl$_3$): δ 7.06-6.92 (m, 4H), 6.81-6.71 (m, 4H), 5.78 (t, J=5.1 Hz, 1H, NH), 3.92 (t, J=5.6 Hz, 2H), 3.31 (q, J=4.1, 5.1 Hz, 2H), 2.78 (d, J=12.6 Hz, 2H), 2.09-1.91 (m, 8H), 1.89-1.74 (m, 12H), 1.72-1.64 (m, 2H), 1.59-1.36 (m, 2H), 1.35-1.23 (m, 2H). $^{13}$C NMR (100 MHz, CDCl$_3$): δ 175.6, 157.0, 154.6, 145.8, 136.2, 135.4, 130.8, 129.7, 127.61 (d, J=278.4 Hz), 115.0, 113.9, 67.4, 44.7, 41.22 (q, J$_{C-F}$=27.3 Hz), 39.7, 39.3, 37.3, 34.6, 34.5, 28.3, 28.1, 26.8, 26.5, 24.3. HRMS-ESI m/z [M+H]$^+$ for C$_{35}$H$_{43}$F3NO$_3$, calculated 582.3190; observed 582.3189.

Example 15. N-(4-(4-(Adamantan-2-ylidene(4-hydroxyphenyl)methyl)phenoxy)butyl)-2-((2-(2,6-dioxopiperidin-3-yl)-1,3-dioxoisoindolin-4-yl)oxy)acetamide

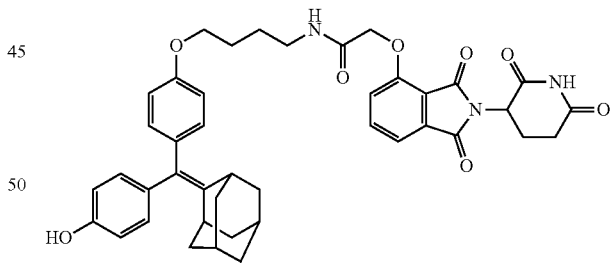

Example 15

2-(2,6-Dioxopiperidin-3-yl)-4-hydroxyisoindoline-1,3-dione. In a three-neck round bottom flask, 3-hydroxyphthalic anhydride (2 g, 12.18 mmol), 3-aminopiperidine-2,6-dione hydrochloride (2.21 g, 13.42 mmol) and potassium acetate (3.59 g, 36.57 mmol) were dissolved in acetic acid (35.5 mL, 0.3 M). After heating to reflux (120° C.) overnight, the solvent was evaporated under reduced pressure to give a grey solid which was washed with water (45 mL). The solid was then subjected to column chromatography (silica gel; MeOH/CH$_2$Cl$_2$, 0 to 1:9) to give a bright yellow powder which was further washed with activated charcoal to afford 2-(2,6-dioxopiperidin-3-yl)-4-hydroxyisoindoline-1,3-dione as a pale yellow solid (1.9 g, 60%). $^1$H NMR (400 MHz, DMSO-d$_6$): δ 10.72 (s, 1H), 10.63 (s, 1H), 7.23-7.17 (m, 1H), 6.89-6.84 (m, 1H), 6.80 (dd, J=5.6, 8.0 Hz, 1H), 4.65-4.58 (m, 1H), 2.49-2.37 (m, 1H), 2.19-2.10 (m, 2H), 1.61-1.52 (m, 1H).

tert-Butyl 2-((2-(2,6-dioxopiperidin-3-yl)-1,3-dioxoisoindolin-4-yl)oxy)acetate. In a round bottom flask, 2-(2,6-dioxopiperidin-3-yl)-4-hydroxyisoindoline-1,3-dione (500 mg, 1.82 mmol) and potassium carbonate (397 mg, 2.87 mmol) were dissolved in DMF (19 mL, 0.1 M). Thereafter, tert-butyl bromoacetate (270 μL, 1.82 mmol) was added and the reaction mixture was stirred for 2 hours at room temperature. Of note, the dialkylated product at the N- and O— positions starts to form at 2 hours, being the predominant product in the mixture after 4 hours. The mixture was diluted with EtOAc (30 mL) and washed once with water (40 mL) then twice with brine (2×30 mL). The organic layer was dried over Na$_2$SO$_4$, filtered and concentrated to afford tert-butyl 2-((2-(2,6-dioxopiperidin-3-yl)-1,3-dioxoisoindolin-4-yl)oxy)acetate as a white solid (485 mg, 68%). $^1$H NMR (400 MHz, CDCl$_3$): δ 7.69 (s, 1H), 7.69-7.64 (m, 1H), 7.51 (d, J=7.3 Hz, 1H), 7.11 (d, J=8.3 Hz, 1H), 4.99-4.93 (m, 1H), 4.79 (s, 2H), 2.96-2.67 (m, 3H), 2.17-2.09 (m, 1H), 1.48 (br s, 9H).

2-((2-(2,6-Dioxopiperidin-3-yl)-1,3-dioxoisoindolin-4-yl)oxy)acetic acid. tert-Butyl 2-((2-(2,6-dioxopiperidin-3-yl)-1,3-dioxoisoindolin-4-yl)oxy)acetate (200 mg, 0.52 mmol) was dissolved in trifluoroacetic acid (5 mL, 0.1 M) at room temperature. After 2 hours, the mixture was diluted with CH$_2$Cl$_2$ (10 mL) and concentrated in vacuo to give 2-((2-(2,6-dioxopiperidin-3-yl)-1,3-dioxoisoindolin-4-yl)oxy)acetic acid as a white solid (242 mg, quantitative). $^1$H NMR (400 MHz, DMSO-d$_6$): δ 11.10 (br s, 1H), 7.77 (br s, 1H), 7.44 (br s, 1H), 7.32 (br s, 1H), 5.10 br (s, 1H), 4.80 (br s, 2H), 2.90 (br s, 1H), 2.62 (br s, 2H), 2.11-1.96 (m, 1H).

2,5-Dioxopyrrolidin-1-yl 2-((2-(2,6-dioxopiperidin-3-yl)-1,3-dioxoisoindolin-4-yl)oxy)acetate. A solution of 2-((2-(2,6-dioxopiperidin-3-yl)-1,3-dioxoisoindolin-4-yl)oxy)acetic acid (160 mg, 0.48 mmol) and N-hydroxysuccimide (60.96 mg, 0.53 mmol) in DMF (2.4 mL) was stirred at 0° C. After 15 minutes, N'-ethylcarbodiimide hydrochloride (101.25 mg, 0.53 mmol) and 4-dimethylaminopyridine (8.8 mg, 0.07 mmol) dissolved in DMF (2.4 mL) were transferred to the reaction flask. The mixture was allowed to warm to room temperature overnight and extracted with EtOAc (3×15 mL), washed with brine and dried on Na$_2$SO$_4$. After filtration, the solvent was evaporated to afford 2,5-dioxopyrrolidin-1-yl 2-((2-(2,6-dioxopiperidin-3-yl)-1,3-dioxoisoindolin-4-yl)oxy)acetate as a white solid (128 mg, quantitative) which was used in the next step without further purification.

N-(4-(4-(Adamantan-2-ylidene(4-hydroxyphenyl)methyl)phenoxy)butyl)-2-((2-(2,6-dioxopiperidin-3-yl)-1,3-dioxoisoindolin-4-yl)oxy)acetamide. To a stirred solution of 4-(adamantan-2-ylidene(4-(4-aminobutoxy)phenyl)methyl)phenol 20 (86 mg, 0.21 mmol) in DMF (1 mL) at 0° C., 2,5-dioxopyrrolidin-1-yl 2-((2-(2,6-dioxopiperidin-3-yl)-1,3-dioxoisoindolin-4-yl)oxy)acetate (83 mg, 0.19 mmol) dissolved in DMF (1 mL) was added. The solution was allowed to warm to room temperature and stirred for 12 h. It was then concentrated and extracted with EtOAc (3×5 mL). The combined organic layers were washed with brine, dried over Na$_2$SO$_4$, concentrated and subjected to column chromatography (silica gel; MeOH/CH$_2$Cl$_2$, 5:95 to 1:5) to give N-(4-(4-(adamantan-2-ylidene(4-hydroxyphenyl)methyl)phenoxy)butyl)-2-((2-(2,6-dioxopiperidin-3-yl)-1,3-dioxoisoindolin-4-yl)oxy)acetamide as a white foam (24 mg, 16%). $^1$H NMR (400 MHz, CDCl$_3$): δ 8.31 br (s, 1H), 7.71 (t, J=9.3 Hz, 1H), 7.53 (d, J=7.6 Hz, 2H), 7.17 (d, J=9.1 Hz, 1H), 7.02-6.92 (m, 4H), 6.79-6.70 (m, 4H), 5.70 (br s, 1H), 4.93 (dd, J=6.6, 12.2 Hz, 1H), 4.63 (s, 2H), 3.97-3.93 (m, 2H), 3.44 (q, J=5.5, 6.1 Hz, 2H), 2.86-2.64 (m, 4H), 2.10-2.05 (m, 1H), 2.00-1.95 (m, 2H), 1.87-1.76 (m, 11H), 1.70-1.66 (m, 4H).

Example 16 was synthesized according to an analogous procedure as described for example 15 from 4-((adamantan-2-ylidene)(4-((6-aminohexyl)oxy)phenyl)methyl)phenol 23.

Example 16. N-(6-(4-(Adamantan-2-ylidene(4-hydroxyphenyl)methyl)phenoxy)hexyl)-2-((2-(2,6-dioxopiperidin-3-yl)-1,3-dioxoisoindolin-4-yl)oxy)acetamide

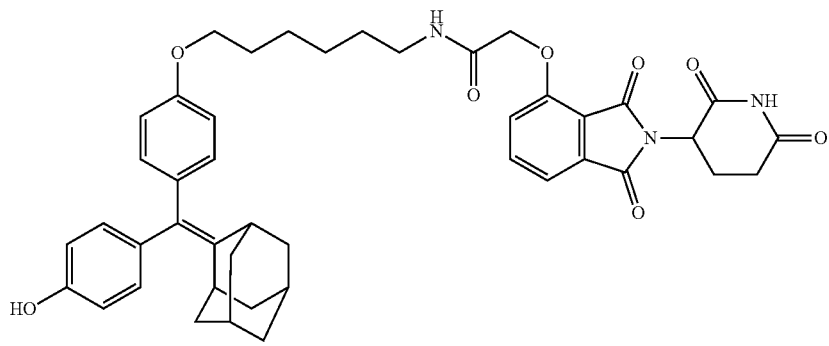 [SMILES: O=C(COc1cccc2c1C(=O)N(C1CCC(=O)NC1=O)C2=O)NCCCCCCOc1ccc(C(=C2C3CC4CC(C3)CC2C4)c2ccc(O)cc2)cc1]

Example 16

$^1$H NMR (400 MHz, CDCl$_3$): δ 8.31 br (s, 1H), 7.71 (t, J=8.4 Hz, 1H), 7.53 (d, J=8.1 Hz, 1H), 7.47-7.43 (m, 1H), 7.17 (d, J=8.3 Hz, 1H), 7.02-6.93 (m, 4H), 6.80-6.70 (m, 4H), 5.49 (br s, 1H), 4.95 (dd, J=5.2, 11.8 Hz, 1H), 4.63 (s, 2H), 3.92 (t, J=6.8 Hz, 2H), 3.42-3.35 (m, 2H), 2.90-2.65 (m, 4H), 2.13-2.07 (m, 1H), 2.00-1.95 (m, 2H), 1.85-1.74 (m, 13H), 1.65-1.59 (m, 3H), 1.48-1.44 (m, 3H). $^{13}$C NMR (100 MHz, CDCl$_3$): δ 171.0, 168.1, 166.9, 166.8, 166.1, 157.3, 154.6, 154.1, 145.9, 137.2, 135.9, 133.7, 130.9, 130.7, 129.7, 119.7, 118.2, 117.6, 114.9, 114.0, 68.2, 67.9, 49.4, 39.7, 39.3, 37.3, 34.5, 31.5, 29.4, 29.3, 28.4, 26.7, 25.9, 22.7.

Example 17. (trans)-N-(4-(4-((6-Hydroxy-2-(4-hydroxyphenyl)benzo[b]thiophen-3-yl)oxy)phenoxy)butyl)-4-(trifluoromethyl)cyclohexanecarboxamide

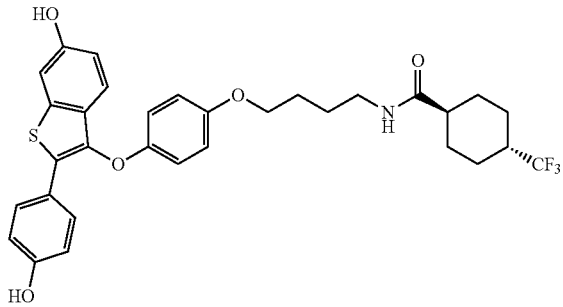 [SMILES: O=C(NCCCCOc1ccc(Oc2c(-c3ccc(O)cc3)sc3cc(O)ccc23)cc1)[C@H]1CC[C@H](C(F)(F)F)CC1]

Example 17

2-(4-Hydroxyphenyl)benzo[b]thiophen-6-ol. To a solution of 6-methoxy-2-(4-methoxyphenyl)benzo[b]thiophene (5 g, 18.5 mmol) in CH$_2$Cl$_2$ (100 ml) at 0° C., BBr$_3$ (74 ml, 74 mmol, 1M in CH$_2$Cl$_2$) was added and the reaction mixture stirred at room temperature for 2 h. The reaction mixture was quenched by addition of cold 10% aqueous NaHCO$_3$ (20 mL) and extracted with EtOAc (3×200 mL). The combined organic layers were washed with saturated aqueous NH$_4$Cl (40 mL), brine (40 mL), dried (Na$_2$SO$_4$), concentrated and purified by flash column chromatography (silica gel; EtOAc/hexanes, 2:8 to 8:2) to afford 2-(4-hydroxyphenyl)benzo[b]thiophen-6-ol (3.6 g, 80%) as a white solid. $^1$H NMR (400 MHz, CD$_3$OD) δ 7.58-7.49 (m, 3H), 7.33 (s, 1H), 7.19 (s, 1H), 6.88-6.80 (m, 3H). $^{13}$C NMR (100 MHz, CD$_3$OD) δ 158.6, 155.9, 142.2, 141.8, 135.7, 128.3, 127.5, 124.9, 118.4, 116.7, 115.4, 108.1.

6-(Methoxymethoxy)-2-(4-(methoxymethoxy)phenyl)benzo[b]thiophene. NaH (714 mg, 29.7 mmol) was placed in a three-neck round bottom flask and a solution of 2-(4-hydroxyphenyl)benzo[b]thiophen-6-ol (3.6 g, 14.8 mmol, dissolved in 20 mL DMF) was slowly added at 0° C. After stirring for 20 min., MOMCl (4.7 ml, 59.2 mmol) was added dropwise while maintaining the temperature at 0° C. The resulting mixture was stirred at room temperature for 12 h and thereafter, diluted with EtOAc (500 mL), washed with 10% aqueous NaHCO$_3$ (60 mL), brine (2×30 mL). The organic layer was dried (Na$_2$SO$_4$) and concentrated. The obtained residue was passed through a short plug of silica gel (EtOAc/hexanes, 3:7) to give a crude bis-MOM intermediate (4 g) which was used as such in the next step. To a solution of the bis-MOM intermediate (4 g, 12 mmol) in CH$_2$Cl$_2$ (40 ml), N-bromoacetamide (1.84 g, 13.3 mmol, dissolved in 10 ml EtOH) was added and the resulting mixture allowed to stir for 1 h. The reaction mixture was filtered and the solid residue was washed with CH$_2$Cl$_2$ (40 mL). The filtrate was concentrated and the obtained residue was purified by flash chromatography (silica gel; EtOAc/hexanes, 2:8 to 8:2) to afford 6-(methoxymethoxy)-2-(4-(methoxymethoxy)phenyl)benzo[b]thiophene (2.8 g, 46%) as a white solid. $^1$H NMR (400 MHz, CDCl$_3$): δ 7.78-7.64 (m, 3H), 7.49 (s, 1H), 7.22-7.11 (m, 3H), 5.29-5.21 (m, 4H), 3.52 (s, 6H). $^{13}$C NMR (100 MHz, CDCl$_3$): δ 157.5, 155.6, 138.5, 135.9, 134.1, 130.7, 126.6, 124.2, 116.2, 116.2, 108.2, 103.7, 94.9, 94.3, 56.1, 56.0.

3-Bromo-6-(methoxymethoxy)-2-(4-(methoxymethoxy)phenyl)benzo[b]thiophene-1-oxide. To a solution of 6-(methoxymethoxy)-2-(4-(methoxymethoxy)phenyl)benzo[b]-thiophene (668 mg, 1.6 mmol) in CH$_2$Cl$_2$ (10 mL) was added 3-(4-nitrophenyl)-2-(phenylsulfonyl)-1,2-oxaziridine (500 mg, 1.6 mmol, preparation: Kummer, D. A.; Li, D.; Dion, A.; Myers, A. G. (2011) A practical, convergent route to the key precursor to the tetracycline antibiotics. Chem. Sci. 2, 1710-1718). After stirring for 12 h, the reaction mixture was concentrated and the obtained residue was purified by flash chromatography (silica gel; EtOAc/hexanes, 2:8 to 9:1) to afford 3-bromo-6-(methoxymethoxy)-2-(4-(methoxymethoxy)phenyl)benzo-[b]thiophene-1-oxide (400 mg, 57%) as a pale yellow solid. $^1$H NMR (400 MHz, CDCl$_3$): δ 7.79 (d, J=8.1 Hz, 2H), 7.67 (s, 1H), 7.57 (d, J=8.6 Hz, 1H), 7.28 (d, J=8.4 Hz, 1H), 7.19 (d, J=8.3 Hz, 2H), 5.29-5.23 (m, 4H), 3.52 (s, 6H). $^{13}$C NMR (100 MHz, CDCl$_3$) δ 158.8, 158.3, 146.0, 143.5, 131.5, 130.9, 125.5, 123.2, 120.4, 116.7, 114.3, 94.8, 94.3, 56.4, 56.2.

tert-Butyl (4-(4-(benzyloxy)phenoxy)butyl)carbamate. A suspension of Cs$_2$CO$_3$ (1.74 g, 5.34 mmol) and 4-((tert-butoxycarbonyl)amino)butyl methanesulfonate (1.43 g, 5.34 mmol, preparation: J. Med. Chem. 2017, 60, 7067-7083) in DMF (14 mL) was stirred at room temperature for 10 minutes and 4-(benzyloxy)phenol (892 mg, 4.45 mol) was added. After stirring for 12 hours at room temperature, the reaction mixture was quenched with 10% aqueous NH$_4$Cl (30 mL) and extracted with EtOAc (3×40 mL). The combined organic layers were washed with brine, dried over Na$_2$SO$_4$, filtered and concentrated to give a mixture of unreacted 4-(benzyloxy)phenol and the title compound. The final product was obtained after passing through a short plug of silica, and used as such in the next step.

tert-Butyl (4-(4-hydroxyphenoxy)butyl)carbamate. A suspension of nickel (II) chloride hexahydrate (1.04 g, 4.78 mmol) and tert-butyl (4-(4-(benzyloxy)phenoxy)butyl)carbamate (813 mg, 2.19 mmol) in methanol (20 mL) was stirred for 10 minutes at 0° C. After addition of sodium borohydride (663 mg, 17.5 mmol), the reaction mixture was stirred for additional 12 hours at room temperature. The crude was filtered through celite and subjected to column chromatography (silica gel; EtOAc/hexanes, 5:95 to 7:3) to give the product as a brownish oil (435 mg, 71%). $^1$H NMR (400 MHz, CDCl$_3$): δ 6.80-6.61 (m, 4H), 6.08 (br s, 1H), 4.73 (br s, 1H), 3.86 (t, J=6.0 Hz, 2H), 3.16 (t, J=6.7 Hz, 2H), 1.74 (m, 2H), 1.62 (m, 2H), 1.45 (s, 9H). $^{13}$C NMR (100 MHz, CDCl$_3$): δ 152.9, 150.1, 116.2, 115.7, 68.3, 40.5, 28.6, 26.9, 26.8.

tert-Butyl (4-(4-((6-(methoxymethoxy)-2-(4-(methoxymethoxy)phenyl)-1-oxidobenzo[b]-thiophen-3-yl)oxy)phenoxy)butyl)carbamate. A suspension of NaH (64 mg, 2.65 mmol) and tert-butyl (4-(4-hydroxyphenoxy)butyl)carbamate (745 mg, 2.65 mmol) in DMF (9 mL) was stirred in an ice bath for 10 minutes when a solution of 3-bromo-6-(methoxymethoxy)-2-(4-(methoxymethoxy)phenyl)benzo[b]thiophene 1-oxide (1.13 g, 2.65 mmol) n DMF (9 mL) was added. After stirring for 12 hours at room temperature, the reaction mixture was quenched with 10% aqueous NaHCO$_3$ (15 mL) and extracted with EtOAc (3×30 mL). The combined organic layers were washed with brine, dried over Na$_2$SO$_4$, filtered and concentrated to give a brown oil. The crude was subjected to column chromatography (silica gel; EtOAc/hexanes, 1:9 to 3:2) to afford the product as a yellow oil (913 mg, 66%). $^1$H NMR (400 MHz, CDCl$_3$): δ 7.73 (d, J=8.8 Hz, 2H), 7.64 (s, 1H), 7.06-6.92 (m, 6H), 6.78 (d, J=9.0 Hz, 2H), 5.27-5.12 (m, 4H), 4.63 (br s, 1H), 3.90

(t, J=6.1 Hz, 2H), 3.47 (s, 3H), 3.45 (s, 3H), 3.17 (d, J=5.9 Hz, 2H), 1.82-1.74 (m, 2H), 1.70-1.61 (m, 2H), 1.43 (s, 9H). $^{13}$C NMR (100 MHz, CDCl$_3$): δ 158.3, 157.5, 156.1, 155.4, 149.1, 148.7, 144.2, 132.2, 129.7, 127.7, 123.8, 123.3, 119.7, 117.9, 116.7, 115.6, 114.9, 94.7, 94.3, 68.1, 56.4, 56.1, 40.3, 28.5, 26.9, 26.7.

tert-Butyl (4-(4-((6-(methoxymethoxy)-2-(4-(methoxymethoxy)phenyl)benzo[b]thiophen-3-yl)oxy)phenoxy)butyl)carbamate. To a solution of tert-butyl (4-(4-((6-(methoxymethoxy)-2-(4-(methoxymethoxy)phenyl)-1-oxidobenzo[b]-thiophen-3-yl)oxy)phenoxy)butyl) carbamate (913 mg, 1.46 mmol) in THF (40 mL), lithium aluminum hydride (1M in THF, 2.19 mL, 2.18 mmol) was added dropwise at 0° C. After stirring for 1 hour at 0° C., 20 mL of water were added to the reaction flask followed by 15 mL of 15% aqueous sodium hydroxide. The resulting emulsion was filtered through celite and extracted with CH$_2$Cl$_2$ (3×30 mL), washed with brine, dried over Na$_2$SO$_4$ and filtered. The concentrated residue was purified by column chromatography (silica gel; EtOAc/hexanes, 1:9 to 1:1) to afford the pure product as a colorless oil (716 mg, 80%). $^1$H NMR (400 MHz, CDCl$_3$): δ 7.68 (d, J=8.9 Hz, 2H), 7.45 (d, J=1.8 Hz, 1H), 7.27 (d, J=8.7 Hz, 1H), 7.02 (d, J=8.9 Hz, 2H), 6.96 (d, J=6.5 Hz, 1H), 6.88 (d, J=9.1 Hz, 1H), 6.77 (d, J=9.1 Hz, 2H), 5.22 (s, 2H), 5.17 (s, 2H), 4.64 (br s, 1H), 3.89 (t, J=6.0 Hz, 2H), 3.51 (s, 3H), 3.47 (s, 3H), 3.20-3.13 (m, 2H), 1.80-1.72 (m, 2H), 1.68-1.60 (m, 2H), 1.44 (s, 9H). $^{13}$C NMR (100 MHz, CDCl$_3$): δ 156.9, 156.1, 155.5, 154.2, 151.8, 140.0, 136.7, 129.2, 128.9, 127.3, 126.2, 122.3, 116.6, 116.5, 115.7, 115.5, 109.0, 95.0, 94.4, 68.1, 56.2, 40.4, 28.5, 27.0, 26.7.

3-(4-(4-Aminobutoxy)phenoxy)-2-(4-hydroxyphenyl)benzo[b]thiophen-6-ol. tert-Butyl (4-(4-((6-(methoxymethoxy)-2-(4-(methoxymethoxy)phenyl)benzo[b]thiophen-3-yl)oxy)phenoxy)butyl)carbamate (296 mg, 0.49 mmol), N-methylimidzole (0.49 mmol) and thiourea (37 mg, 0.49 mmol) were placed in a three-neck round bottom flask with acetonitrile (9 mL). The slurry was degassed (vacuum/nitrogen purges), cooled to 5° C. and iodotrimethylsilane (610 μL, 4.37 mmol) was added dropwise. The mixture was then allowed to warm to room temperature and the flask was wrapped with aluminum foil to avoid exposure to light (light promotes side reactions). The reaction was heated to 65° C. for 12 hours, after which it was diluted with MeOH (20 mL) and filtered through celite. The final product was obtained after passing through a short plug of silica, and used as such in the next step.

(trans)-N-(4-(4-((6-Hydroxy-2-(4-hydroxyphenyl)benzo[b]thiophen-3-yl)oxy)phenoxy)-butyl)-4-(trifluoromethyl)cyclohexanecarboxamide. The title compound was synthesized by reaction of 3-(4-(4-aminobutoxy)phenoxy)-2-(4-hydroxyphenyl)benzo[b]thiophen-6-ol with (trans)-2,5-dioxopyrrolidin-1-yl-4-(trifluoromethyl)cyclohexane-1-carboxylate in an analogous procedure to the one described for example 1. $^1$H NMR (400 MHz, CD$_3$OD): δ 7.55 (d, J=8.8 Hz, 1H), 7.21-7.11 (m, 1H), 6.85-6.63 (m, 9H), 3.89 (t, J=6.2 Hz, 2H), 3.22 (q, J=6.7 Hz, 2H), 2.19-2.07 (m, 2H), 2.01-1.95 (m, 2H), 1.93-1.85 (m, 2H), 1.77-1.69 (m, 2H), 1.68-1.61 (m, 2H), 1.55-1.45 (m, 3H), 1.39-1.29 (m, 2H). $^{13}$C NMR (100 MHz, CD$_3$OD): δ 178.1, 158.3, 156.8, 155.6, 153.1, 140.7, 138.0, 130.4, 129.7, 128.6, 127.7, 127.1, 122.9, 117.2, 116.6, 115.4, 108.8, 69.0, 45.4, 42.30 (q, $J_{C-F}$=26.2 Hz), 39.6, 29.0, 27.8, 27.7, 27.1, 25.4.

Example 18. 4-(2-(2-(2-(4-(Adamantan-2-ylidene(4-hydroxyphenyl)methyl)phenoxy)-ethoxy)ethoxy)ethoxy)-2-(2,6-dioxopiperidin-3-yl)isoindoline-1,3-dione

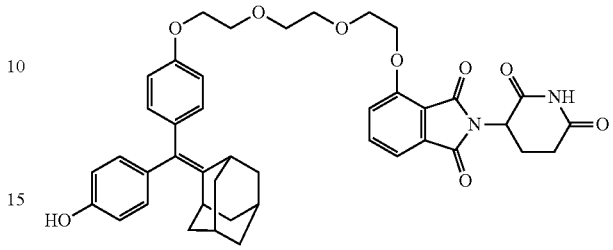

Example 18

4-(Adamantan-2-ylidene(4-(methoxymethoxy)phenyl)methyl)phenol. A suspension of NaH (145 mg, 6.04 mmol) and 4,4'-((adamantan-2-ylidene)methylene)diphenol 18 (1 g, 3.01 mmol) in DMF (5 mL) was stirred in an ice bath for 10 minutes when chloromethyl methyl ether chloride (228 μL, 3.01 mmol) was added. After stirring for 12 h at room temperature, the reaction mixture was quenched with 10% NaHCO$_3$ (10 mL) and extracted with EtOAc (3×15 mL). The combined organic layers were washed with brine, dried over Na$_2$SO$_4$, filtered and concentrated to give a mixture of unreacted starting material, dialkylated product and the desired product. The crude was subjected to column chromatography (silica gel; EtOAc/hexanes, 2:8 to 7:3) to afford the product as a white solid (456 mg, 46%). $^1$H NMR (400 MHz, CDCl$_3$): δ 7.06-6.95 (m, 4H), 6.97-6.88 (m, 2H), 6.74-6.70 (m, 2H), 5.15 (s, 2H), 3.49 (s, 3H), 2.77 (br s, 1H), 2.68 (br s, 1H), 1.99 (br s, 2H), 1.89-1.71 (m, 10H), 1.61-1.53 (m, 1H). $^{13}$C NMR (100 MHz, CDCl$_3$): δ 155.5, 153.9, 146.2, 145.3, 137.23, 137.16, 136.03, 135.95, 130.9, 130.7, 130.5, 129.6, 115.8, 114.9, 94.7, 56.2, 39.7, 37.3, 34.5, 34.3, 33.9, 28.4, 21.8.

2-(2-(2-(4-(Adamantan-2-ylidene(4-(methoxymethoxy)phenyl)methyl)phenoxy)-ethoxy)ethoxy)ethyl 4-methylbenzenesulfonate. The title compound was synthesized by reaction of 4-(adamantan-2-ylidene(4-(methoxymethoxy)phenyl)methyl)phenol with TsOCH$_2$CH$_2$OCH$_2$CH$_2$OCH$_2$CH$_2$OTs (Bioorg. Med. Chem. Lett. 2017, 24, 686-692) using Cs$_2$CO$_3$ as base is DMF. $^1$H NMR (400 MHz, CDCl$_3$): δ 7.80 (d, J=7.8 Hz, 2H), 7.32 (d, J=7.7 Hz, 2H), 7.07-6.99 (m, 4H), 6.93 (d, J=7.9 Hz, 2H), 6.80 (d, J=7.8 Hz, 2H), 5.15 (s, 2H), 4.16 (s, 2H), 4.07 (s, 2H), 3.80 (s, 2H), 3.69 (s, 2H), 3.64 (s, 2H), 3.60 (s, 2H), 3.48 (s, 3H), 2.78 (s, 1H), 2.69 (s, 1H), 2.41 (s, 3H), 2.02-1.96 (m, 2H), 1.90-1.74 (m, 10H). $^{13}$C NMR (100 MHz, CDCl$_3$): δ 157.1, 155.6, 146.1, 145.2, 144.9, 137.13, 137.06, 136.1, 136.0, 133.1, 130.6, 130.4, 129.9, 129.6, 128.1, 115.7, 114.1, 94.6, 70.9, 70.8, 69.9, 69.4, 68.8, 67.4, 56.1, 39.7, 37.3, 34.5, 34.5, 34.2, 33.9, 28.3, 21.8, 21.7.

4-(2-(2-(2-(4-(Adamantan-2-ylidene(4-hydroxyphenyl)methyl)phenoxy)ethoxy)ethoxy)-ethoxy)-2-(2,6-dioxopiperidin-3-yl)isoindoline-1,3-dione. A suspension of 2-(2,6-dioxopiperidin-3-yl)-4-hydroxyisoindoline-1,3-dione (40 mg, 0.15 mmol) and K$_2$CO$_3$ (30 mg, 0.22 mmol) in DMF (2 mL) was placed in a round bottom flask and stirred for 10 minutes at room temperature. 2-(2-(2-(4-(adamantan-2-ylidene(4-(methoxymethoxy)phenyl)methyl)-phenoxy)

ethoxy)ethoxy)ethyl 4-methylbenzenesulfonate (97 mg, 0.15 mmol) was then added to the reaction flask and heated to reflux (80° C.) for 2 hours, after which the reaction mixture was diluted with EtOAc (10 mL) and extracted with EtOAc (3×5 mL). The combined organic layers were washed with brine, dried ($Na_2SO_4$), filtered and concentrated to give a brown oil which was purified by column chromatography (silica gel; EtOac/hexanes, 2:3 to 9:1) to afford an intermediate as a white foam (16 mg, 14%). The MOM and BOC groups were cleaved from the intermediate following the TMSI protocol described above. $^1$H NMR (400 MHz, $CD_3OD$): δ 7.69 (s, 1H), 7.43-7.38 (m, 2H), 7.01-6.87 (m, 5H), 6.81-6.77 (m, 2H), 6.70-6.65 (m, 2H), 5.06 (dd, J=5.4, 12.5 Hz, 1H), 4.36-4.33 (m, 2H), 4.08-4.03 (m, 2H), 3.93-3.88 (m, 2H), 3.84-3.80 (m, 2H), 3.80-3.75 (m, 2H), 3.73-3.68 (m, 2H), 2.82-2.62 (m, 4H), 2.08-2.04 (m, 1H), 1.99-1.94 (m, 2H), 1.90-1.83 (m, 9H), 1.79-1.74 (m, 2H). $^{13}$C NMR (101 MHz, $CD_3OD$): δ 174.6, 171.4, 168.6, 167.3, 158.5, 157.8, 156.7, 146.2, 145.2, 137.9, 137.3, 135.8, 135.1, 132.4, 131.7, 131.5, 131.2, 121.0, 118.3, 116.6, 115.7, 115.1, 72.1, 71.8, 70.9, 70.5, 68.6, 50.4, 40.6, 38.3, 35.8, 35.5, 34.8, 32.2, 29.7, 23.6, 23.6, 22.7.

Example 19 was synthesized by analogous procedures as used for the synthesis of example 18 except $TsOCH_2CH_2OCH_2CH_2OTs$ (Chem. Commun. 2017, 53, 8751-8754) replaced $TsOCH_2CH_2OCH_2CH_2OCH_2CH_2OTs$ in the second step.

Example 19. 4-(2-(2-(4-(Adamantan-2-ylidene(4-hydroxyphenyl)methyl)phenoxy)-ethoxy)ethoxy)-2-(2,6-dioxopiperidin-3-yl)isoindoline-1,3-dione

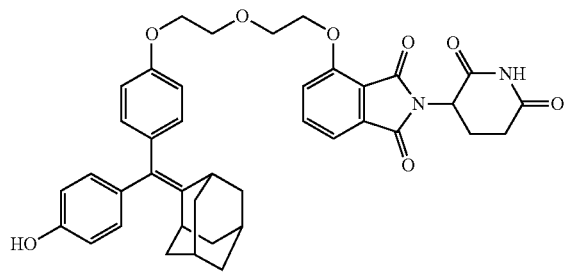 [SMILES: O=C1CCC(N2C(=O)c3cccc(OCCOCCOc4ccc(C(=C5C6CC7CC(C6)CC5C7)c5ccc(O)cc5)cc4)c3C2=O)C(=O)N1]

Example 19

$^1$H NMR (400 MHz, $CDCl_3$): δ 8.04 (s, 1H), 7.62 (t, J=7.8 Hz, 1H), 7.45 (d, J=7.9 Hz, 1H), 7.06-6.90 (m, 5H), 6.83-6.65 (m, 4H), 4.98-4.88 (m, 1H), 4.38-4.31 (m, 2H), 4.13-4.05 (m, 2H), 4.02-3.88 (m, 4H), 2.91-2.61 (m, 4H), 2.12-2.03 (m, 1H), 2.01-1.93 (m, 2H), 1.87-1.69 (m, 10H), 1.65-1.52 (m, 1H). $^{13}$C NMR (100 MHz, $CDCl_3$): δ 171.1, 168.2, 167.1, 165.8, 162.8, 157.0, 156.6, 154.2, 145.9, 145.0, 136.6, 136.2, 135.7, 133.8, 130.8, 130.6, 130.4, 129.7, 119.8, 117.5, 116.4, 114.9, 114.1, 70.5, 69.7, 69.6, 67.6, 49.3, 39.7, 37.3, 36.6, 34.5, 34.3, 33.9, 31.5, 28.3.

Example 20. (trans)-N-(4-(4-((5-Hydroxy-2-(4-hydroxyphenyl)-3-methyl-1H-indol-1-yl)methyl)phenoxy)butyl)-4-(trifluoromethyl)cyclohexanecarboxamide

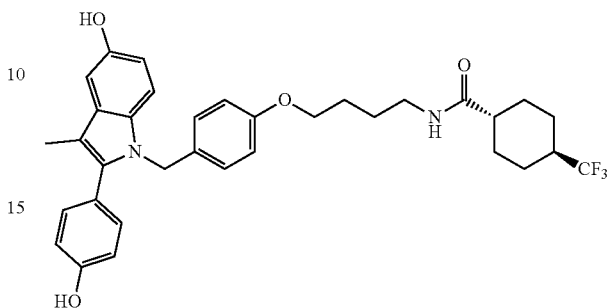

Example 20

5-(Benzyloxy)-2-(4-(benzyloxy)phenyl)-3-methyl-1H-indole. This protocol was modified from J. Med. Chem. 2001, 44, 1654-1657. A 50-mL 3-neck flask was charged with 4'-benzyloxy-2-bromophenylpropiophenone (1 g, 3.13 mmol) 4-benzyloxyaniline hydrochloride (1.7 g, 7.21 mmol), triethylamine (1.04 mL, 7.21 mmol) and 25 mL of DMF. The reaction was heated at reflux for 2.5 hours, cooled to rt and partitioned between EtOAc (3×80 mL) and $H_2O$ (70 mL). The combined EtOAc fractions were washed with brine (80 mL) and dried over $Na_2SO_4$. The obtained residue was purified by column chromatography (silica gel, EtOAc/Hex, 1:9 to 2:3) to afford the product as a pale yellow powder (845 mg, 65%). $^1$H NMR (400 MHz, $CDCl_3$) δ 7.95 (br s, 1H, NH), 7.67-7.58 (m, 6H), 7.57-7.50 (m, 5H), 7.51-7.44 (m, 2H), 7.37 (d, J=10.4 Hz, 1H), 7.21 (d, J=6.9 Hz, 2H), 7.07 (d, J=8.2 Hz, 1H), 5.28 (s, 2H), 5.26 (s, 2H), 2.53 (s, 3H).

tert-Butyl (4-(4-(hydroxymethyl)phenoxy)butyl)carbamate. A suspension of $Cs_2CO_3$ (1.31 g, 4.02 mmol) and 4-(hydroxymethyl)phenol (500 mg, 4.02 mmol) in DMF (20 mL) was stirred at room temperature for 10 minutes and 4-((tert-Butoxycarbonyl)amino)butyl methanesulfonate (1.08 g, 4.02 mmol) was added. After stirring for 12 hours at room temperature, the reaction mixture was quenched with 10% aqueous $NH_4Cl$ (80 mL) and extracted with EtOAc (3×70 mL). The combined organic layers were washed with brine, dried over $Na_2SO_4$, filtered and concentrated to give a yellow oil. The final product was obtained after column chromatography (silica gel, MeOH/$CH_2Cl_2$, 0:1 to 1:9) which provided a colorless oil (804 mg, 68%). $^1$H NMR (400 MHz, $CD_3OD$) δ 7.25 (d, J=7.9 Hz, 2H), 6.88 (d, J=8.0 Hz, 2H), 4.51 (s, 2H), 3.97 (t, J=6.0 Hz, 2H), 3.10 (q, J=6.1 Hz, 2H), 1.81-1.73 (m, 2H), 1.67-1.59 (m, 2H), 1.44 (s, 9H). Exchangeable protons (NH, OH) not observed.

tert-Butyl (4-(4-(bromomethyl)phenoxy)butyl)carbamate. The title compound was prepared as described in Tetrahedron Lett. 2016, 57, 168-171. To a suspension of tert-butyl (4-(4-(hydroxymethyl)phenoxy)butyl)carbamate (240 mg, 0.81 mmol) and potassium bromide (145 mg, 1.21 mmol) in acetonitrile (6 mL), phosphorous pentoxide (101 mg, 1.21 mol) was added. After stirring for 3 h at rt, the reaction mixture was washed with $H_2O$ (20 mL) and extracted with EtOAc (3×30 mL). The organic fraction was then washed with brine and dried over $Na_2SO_4$. The solvent was evaporated to give a yellow oil which was subjected to column chromatography (silica gel, EtOAc/Hex, 1:4 to 3:2) to give a white semi-solid (102 mg, 35%). $^1$H NMR (400 MHz, CDCl$_3$) δ 7.29 (d, J=8.3 Hz, 2H), 6.83 (d, J=8.2 Hz, 2H), 4.48 (s, 2H), 3.95 (t, J=5.5 Hz, 2H), 3.21-3.13 (m, 2H), 1.84-1.75 (m, 2H), 1.69-1.60 (m, 2H), 1.43 (s, 9H). Exchangeable proton (NH) not observed. $^{13}$C NMR (100 MHz, CDCl$_3$) δ 159.1, 156.1, 130.5, 130.0, 114.8, 67.7, 40.4, 34.1, 28.5, 26.9, 26.6.

tert-Butyl (4-(4-((5-(benzyloxy)-2-(4-(benzyloxy)phenyl)-3-methyl-1H-indol-1-yl)methyl)phenoxy)butyl)carbamate. NaH (39 mg, 1.6 mmol) was placed in a 25-mL three-neck round bottom flask and a solution of 5-(benzyloxy)-2-(4-(benzyloxy)phenyl)-3-methyl-1H-indole (562 mg, 1.33 mmol) in DMF (5 mL) was slowly added at 0° C. After stirring for 30 min., a solution of tert-butyl (4-(4-(bromomethyl)phenoxy)butyl)carbamate (768 mg, 2018 mmol) in DMF (5 mL) was added dropwise while maintaining the temperature at 0° C. The resulting mixture was stirred at room temperature for 12 h and partitioned between H$_2$O (25 mL) and EtOAc (3×30 mL). The organic layer was dried (Na$_2$SO$_4$) and concentrated. The resulting residue was purified by column chromatography (silica gel, EtOAc/Hex, 1:9 to 1:4) to afford the pure product as a yellow oil (537 mg, 73%). $^1$H NMR (400 MHz, CDCl$_3$) δ 7.49-7.45 (m, 2H), 7.45-7.41 (m, 2H), 7.40-7.33 (m, 5H), 7.33-7.27 (m, 2H), 7.22-7.20 (m, 1H), 7.13 (s, 1H), 7.08-7.03 (m, 1H), 7.03-6.96 (m, 2H), 6.89-6.81 (m, 3H), 6.71 (d, J=7.8 Hz, 2H), 5.11 (s, 2H), 5.09 (s, 2H), 5.07 (s, 2H), 3.88 (t, J=5.5 Hz, 2H), 3.18-3.11 (m, 2H), 2.23 (s, 3H), 1.79-1.71 (m, 2H), 1.68-1.56 (m, 2H), 1.42 (s, 9H). Exchangeable proton (NH) not observed.

tert-Butyl (4-(4-((5-hydroxy-2-(4-hydroxyphenyl)-3-methyl-1H-indol-1-yl)methyl)phenoxy)butyl)carbamate. A 10-mL three-neck flask was charged with tert-butyl (4-(4-((5-(benzyloxy)-2-(4-(benzyloxy)phenyl)-3-methyl-1H-indol-1-yl)methyl)phenoxy)butyl)carbamate (150 mg, 0.21 mmol) and MeOH (4 mL). The suspension was purged with nitrogen gas for five minutes followed by addition of Pd(OH)$_2$/C (30 mg, 20% w/w) under inert conditions. The resulting black suspension was subjected to three hydrogen-vacuum cycles and stirred for 3.5 hours at rt under three hydrogen balloons. The catalyst was removed by filtration through a short pad of Celite and the filtrate was purified on column chromatography (silica gel, EtOAc/Hex, 3:7 to 3:2) to give the product as a yellow oil (69 mg, 63%). $^1$H NMR (400 MHz, CDCl$_3$) δ 7.11 (d, J=8.4 Hz, 2H), 7.02-6.96 (m, 2H), 6.85 (d, J=8.3 Hz, 2H), 6.77 (d, J=8.4 Hz, 2H), 6.74-6.69 (m, 1H), 6.65 (d, J=8.5 Hz, 2H), 5.04 (s, 2H), 4.75 (br s, 1H, NH), 3.81 (t, J=5.8 Hz, 2H), 3.17-3.11 (m, 2H), 2.15 (s, 3H), 1.73-1.65 (m, 2H), 1.62-1.55 (m, 2H), 1.44 (s, 9H). Exchangeable protons (2×OH) not observed.

1-(4-(4-Aminobutoxy)benzyl)-2-(4-hydroxyphenyl)-3-methyl-1H-indol-5-ol. To a solution of tert-butyl (4-(4-((5-hydroxy-2-(4-hydroxyphenyl)-3-methyl-1H-indol-1-yl)methyl)phenoxy)butyl)carbamate (169 mg, 0.33 mmol) in CH$_2$Cl$_2$ (2 mL) trifluoroacetic acid (TFA, 1 mL) was added at 0° C. After stirring at 0° C. for 0.5 hours, TFA was removed by passing a stream of compressed air and co-evaporation with acetonitrile. The concentrated residue was subjected to flash column chromatography (silica gel; MeOH/CH$_2$Cl$_2$, 0:10 to 2:8) to give the product as a yellow oil (103 mg, 76%). $^1$H NMR (400 MHz, CD$_3$OD) δ 7.15-7.09 (m, 2H), 7.04-6.98 (m, 1H), 6.94-6.90 (m, 1H), 6.87-6.81 (m, 2H), 6.77-6.63 (m, 5H), 5.06 (s, 2H), 3.90 (t, J=5.7 Hz, 2H), 3.00-2.92 (m, 2H), 2.16 (s, 3H), 1.83-1.74 (m, 4H). Exchangeable protons (2×OH, NH$_2$) not observed.

(trans)-N-(4-(4-((5-Hydroxy-2-(4-hydroxyphenyl)-3-methyl-1H-indol-1-yl)methyl)phenoxy)butyl)-4-(trifluoromethyl)cyclohexanecarboxamide. The title compound was synthesized by reaction of 1-(4-(4-aminobutoxy)benzyl)-2-(4-hydroxyphenyl)-3-methyl-1H-indol-5-ol with (trans)-2,5-dioxopyrrolidin-1-yl-4-(trifluoromethyl)cyclohexane-1-carboxylate in an analogous procedure to the one described for example 1. $^1$H NMR (400 MHz, CD$_3$OD) δ 7.88 (br s, 1H, OH), 7.14 (d, J=8.3 Hz, 2H), 7.03 (d, J=8.5 Hz, 1H), 6.94 (s, 1H), 6.86 (d, J=8.1 Hz, 2H), 6.78 (d, J=8.4 Hz, 2H), 6.72 (d, J=8.4 Hz, 2H), 6.71-6.64 (m, 1H), 6.43 (br s, 1H, OH), 5.10 (s, 2H), 3.91 (t, J=6.0 Hz, 2H), 3.23 (q, J=6.8, 6.2 Hz, 2H), 2.19 (s, 3H), 2.16-2.07 (m, 1H), 2.00 (d, J=11.5 Hz, 2H), 1.90 (d, J=11.2 Hz, 2H), 1.78-1.70 (m, 2H), 1.69-1.62 (m, 2H), 1.56-1.45 (m, 2H), 1.41-1.30 (m, 3H). Exchangeable proton (NH) not observed. $^{13}$C NMR (100 MHz, CD$_3$OD) δ 178.1, 159.3, 158.4, 151.5, 139.9, 133.1, 132.8, 132.3, 130.7 (d, $J_{C-F}$=48.1 Hz), 128.4, 124.6, 123.1, 116.2, 115.4, 112.1, 111.6, 108.5, 103.9, 68.5, 45.4, 42.31 (q, $J_{C-F}$=27.7, 27.0 Hz), 39.9, 29.0, 27.7, 27.1, 25.3, 9.6.

Example 21. N-(4-(4-((5-Hydroxy-2-(4-hydroxyphenyl)-3-methyl-1H-indol-1-yl)methyl)phenoxy)butyl)adamantane-1-carboxamide

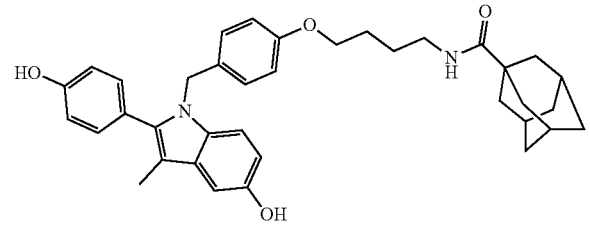 [SMILES: Cc1c(-c2ccc(O)cc2)n(Cc2ccc(OCCCCNC(=O)C34CC5CC(CC(C5)C3)C4)cc2)c2ccc(O)cc12]

Example 21

The title compound was synthesized by reaction of 1-(4-(4-aminobutoxy)benzyl)-2-(4-hydroxyphenyl)-3-methyl-1H-indol-5-ol with (1S,3s)-2,5-dioxopyrrolidin-1-yl adamantane-1-carboxylate in an analogous procedure to the one described for example 1. $^1$H NMR (400 MHz, CD$_3$OD) δ 8.75 (br s, 1H, OH), 8.44 (br s, 1H, OH), 7.54 (dd, J=8.3, 4.5 Hz, 1H), 7.15 (d, J=8.2 Hz, 2H), 7.03 (d, J=8.7 Hz, 1H), 6.93 (br s, 1H, NH), 6.86 (d, J=8.5 Hz, 2H), 6.80-6.71 (m, 4H), 6.67 (d, J=8.8 Hz, 1H), 5.11 (s, 2H), 3.93 (t, J=5.9 Hz, 2H), 3.23 (t, J=6.7 Hz, 2H), 2.18 (s, 3H), 2.01-1.96 (m, 4H), 1.85-1.81 (m, 6H), 1.77-1.68 (m, 9H). $^{13}$C NMR (100 MHz, CD$_3$OD) δ 180.8, 159.3, 158.4, 152.0, 151.5, 141.0, 139.9, 136.3, 133.1, 132.8, 132.3, 130.9, 129.8, 124.6, 122.1, 116.2, 115.4, 112.1, 111.6, 108.5, 103.9, 68.5, 40.2, 40.0, 37.6, 29.6, 27.7, 27.1, 9.6.

Example 22. (trans)-N-(4-(4-(6-Hydroxy-2-phenyl-1,2,3,4-tetrahydronaphthalen-1-yl)phenoxy)butyl)-4-(trifluoromethyl)cyclohexanecarboxamide

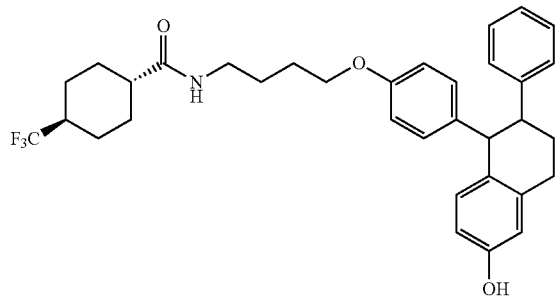 [SMILES: O=C(NCCCCOc1ccc(C2c3ccc(O)cc3CCC2c2ccccc2)cc1)[C@H]1CC[C@H](C(F)(F)F)CC1]

Example 22

4-(4-(Benzyloxy)phenyl)-7-methoxy-1,2-dihydronaphthalene. The Grignard reagent was synthesized following the procedure described in Res. Chem. Intermed. 2009, 35, 615-623. A suspension of Mg turnings (321 mg, 13.38 mmol) with a crystal of iodine in THF (7 mL) was placed in ultrasonic bath at 45° C. for 30 minutes. The flask was then moved to a silicon oil bath and stirred at 60° C. for 40 minutes, resulting in a change of color (from purple to pale yellow). A solution of 4-benzyloxybromobenzene (3.2 g, 12.17 mmol, prepared as in Chem. Eur. J. 2016, 22, 16721-16276) in THF (10 mL) was then added dropwise at 60° C. After stirring at 60° C. for 45 minutes the solution became light brown as a result of the formation of the Grignard reagent, after which the reaction mixture was cooled to 40° C. A solution of 6-methoxy-1-tetralone (4.3 g, 24.40 mmol) in THF (15 mL) was added drop by drop to the previous solution. The reaction was kept at 65° C. for 3 h, thereafter cooled to 0° C. and quenched with HCl (1M, 200 mL, pH 2). The aqueous layer was extracted with $CH_2Cl_2$ (3×100 mL) and the combined organic fractions were washed with brine (200 mL) and dried ($Na_2SO_4$). After removal of the solvent the mixture was subjected to column chromatography (silica gel, $CH_2C_2$/Hex, 1:4 to 9:1) to provide the product as a white solid (1.12 g, 28%). $^1$H NMR (400 MHz, $CDCl_3$) δ 7.49-7.44 (m, 2H), 7.43-7.38 (m, 2H), 7.38-7.29 (m, 1H), 7.29-7.25 (m, 2H), 7.00-6.94 (m, 3H), 6.77 (d, J=2.8 Hz, 1H), 6.64 (dd, J=8.7, 2.4 Hz, 1H), 5.91 (t, J=4.5 Hz, 1H), 5.10 (s, 2H), 3.80 (s, 3H), 2.81 (t, J=7.7 Hz, 2H), 2.40-2.33 (m, 2H). $^{13}$C NMR (100 MHz, $CDCl_3$) δ 158.7, 158.2, 139.0, 138.8, 137.3, 133.9, 129.9, 128.7, 128.1, 127.6, 126.7, 124.6, 114.7, 113.9, 110.8, 70.2, 55.4, 29.0, 23.6.

4-(4-(Benzyloxy)phenyl)-3-bromo-7-methoxy-1,2-dihydronaphthalene. A solution of 4-(4-(benzyloxy)phenyl)-7-methoxy-1,2-dihydronaphthalene (700 mg, 2.04 mmol) and pyridinium perbromide (916 mg, 2.86 mmol) in THF (15 mL) was stirred at rt for 3 hours. Of note, longer reaction times lead to formation of polybrominated by-products that are difficult to purify by column chromatography. Because the product and starting material have the same $R_f$ on TLC ($R_f$=0.22, EtOAc/Hex 5:95), the reaction was monitored by HPLC-MS (APCI-positive mode). The formation of the product is evident by two peaks at m/z 420 and 422 showing a characteristic bromine isotope pattern. Alternatively, the reaction can be monitored by NMR, particularly by disappearance of the vinylic proton at 55.91 ppm. After reaction completion the mixture was quenched with saturated aqueous $NaHCO_3$ (60 mL) and extracted with $CH_2Cl_2$ (3×70 mL). The combined organic fractions were washed with brine (80 mL), dried over $Na_2SO_4$ and purified by column chromatography (silica gel, $CH_2C_2$/Hex, 3:7 to 9:1) to give the mono-brominated product as a yellow oil (591 mg, 68%). $^1$H NMR (400 MHz, $CDCl_3$) δ 7.54-7.50 (m, 2H), 7.48-7.43 (m, 2H), 7.43-7.35 (m, 1H), 7.21 (d, J=8.7 Hz, 2H), 7.09 (d, J=8.7 Hz, 2H), 6.76 (d, J=2.1 Hz, 1H), 6.66 (d, J=8.5 Hz, 1H), 6.60 (dd, J=8.5, 2.5 Hz, 1H), 5.14 (s, 2H), 3.81 (s, 3H), 3.05-2.95 (m, 4H).

4-(4-(Benzyloxy)phenyl)-7-methoxy-3-phenyl-1,2-dihydronaphthalene. A 25-mL three-neck flask was charged with Tetrakis(triphenylphosphine)palladium(0) (13 mg, 3 mol %), phenylboronic acid (60 mg, 0.49 mmol) and sodium carbonate (113 mg, 1.07 mmol). A solution of 4-(4-(benzyloxy)phenyl)-3-bromo-7-methoxy-1,2-dihydronaphthalene (126 mg, 0.38 mmol) in DMF (5 mL) was added and the reaction mixture was heated at 100° C. for 3.5 hours. The solution was partitioned between $H_2O$ and $CH_2Cl_2$ (3×20 mL) and the combined organic fractions were washed with brine (35 mL) and dried over $Na_2SO_4$. After solvent evaporation under reduced pressure, the mixture was subjected to column chromatography (silica gel, $CH_2Cl_2$/Hex, 3:7 to 9:1) to afford a yellow oil (70 mg, 56%). $^1$H NMR (400 MHz, $CDCl_3$) δ 7.45-7.30 (m, 5H), 7.13-7.08 (m, 2H), 7.06-7.00 (m, 3H), 6.98 (d, J=8.5 Hz, 2H), 6.84 (d, J=8.5 Hz, 2H), 6.79-6.73 (m, 2H), 6.60 (dd, J=8.5, 2.4 Hz, 1H), 5.01 (s, 2H), 3.79 (s, 3H), 2.97-2.91 (m, 2H), 2.81-2.74 (m, 2H). $^{13}$C NMR (100 MHz, $CDCl_3$) δ 158.6, 157.5, 143.4, 137.8, 137.2, 134.9, 134.5, 132.5, 132.3, 130.6, 128.6, 128.4, 128.0, 127.7, 127.6, 125.8, 115.3, 114.5, 113.3, 110.9, 70.1, 55.4, 30.9, 29.1.

4-(6-Methoxy-2-phenyl-1,2,3,4-tetrahydronaphthalen-1-yl)phenol. A 10-mL three-neck flask was charged with 4-(4-(benzyloxy)phenyl)-7-methoxy-3-phenyl-1,2-dihydronaphthalene (270 mg, 0.64 mmol) and MeOH (4 mL). The suspension was purged with nitrogen gas for five minutes followed by addition of Pd(OH)$_2$/C (27 mg, 10% w/w) under inert conditions. The resulting black suspension was subjected to three hydrogen-vacuum cycles and stirred for 12 hours at rt under three hydrogen balloons. The catalyst was removed by filtration through a short pad of Celite and the filtrate was purified on column chromatography (silica gel, EtOAc/Hex, 1:4 to 3:2) to give a mixture of diastereomers (97 mg, 51%, dr ratio 1:1 based on NMR). $^1$H NMR (400 MHz, $CDCl_3$) δ 7.18-7.14 (m, 3H), 7.00-6.92 (m, 2H), 6.87 (d, J=8.4 Hz, 1H), 6.85-6.78 (m, 2H), 6.78-6.72 (m, 5H), 6.71-6.65 (m, 3H), 6.62 (dd, J=8.5, 2.8 Hz, 1H), 6.46 (d, J=8.6 Hz, 2H), 6.28 (d, J=8.6 Hz, 2H), 4.74 (br s, 1H, OH), 4.63 (br s, 1H, OH), 4.24 (d, J=5.0 Hz, 1H), 4.00 (t, J=6.6 Hz, 1H), 3.82 (s, 3H), 3.78 (s, 3H), 3.40-3.32 (m, 1H), 3.11-3.02 (m, 2H), 2.91-2.75 (m, 3H), 2.24-2.04 (m, 3H), 1.89-1.69 (m, 6H).

tert-Butyl (4-(4-(6-methoxy-2-phenyl-1,2,3,4-tetrahydronaphthalen-1-yl)phenoxy)-butyl)carbamate. A suspension of $Cs_2CO_3$ (77 mg, 0.24 mmol), potassium carbonate (32 mg, 0.24 mmol) and 4-(6-methoxy-2-phenyl-1,2,3,4-tetrahydronaphthalen-1-yl)phenol (155 mg, 0.47 mmol) in DMF (2 mL) was stirred at room temperature for 10 minutes. A solution of 4-((tert-butoxycarbonyl)amino)butyl methanesulfonate (125 mg, 0.47 mmol) in DMF (3 mL) was then added. After stirring for 12 hours at 60° C., the reaction mixture was quenched with 10% aqueous $NH_4Cl$ (30 mL) and extracted with EtOAc (3×30 mL). The combined organic layers were washed with brine, dried over $Na_2SO_4$, filtered and concentrated to give a yellow oil. The mixture was subjected to column chromatography (silica gel, EtOAc/Hex, 1:4 to 3:2) to provide a mixture of diastereomers (172 mg, 74%, dr ratio 1:1 based on NMR). $^1$H NMR (400 MHz, CDCl$_3$) δ 7.19-7.15 (m, 4H), 7.01 (d, J=8.6 Hz, 2H), 6.95 (d, J=8.5 Hz, 1H), 6.88 (d, J=8.5 Hz, 2H), 6.85-6.75 (m, 8H), 6.71-6.67 (m, 3H), 6.65-6.61 (m, 1H), 6.56-6.47 (m, 2H), 6.36-6.25 (m, 2H), 4.25 (t, J=5.9 Hz, 1H), 4.03-3.93 (m, 3H), 3.82 (s, 3H), 3.79 (s, 3H), 3.37 (dd, J=12.1, 6.0 Hz, 1H), 3.18 (dd, J=12.9, 6.7 Hz, 3H), 3.07 (d, J=16.0 Hz, 2H), 2.94-2.79 (m, 2H), 2.15-2.08 (m, 1H), 1.92-1.71 (m, 10H), 1.69-1.57 (m, 4H), 1.47 (s, 18H).

4-(4-(6-Methoxy-2-phenyl-1,2,3,4-tetrahydronaphthalen-1-yl)phenoxy)butan-1-amine. To a solution of tert-butyl (4-(4-(6-methoxy-2-phenyl-1,2,3,4-tetrahydronaphthalen-1-yl)phenoxy)butyl)carbamate (275 mg, 0.55 mmol) in CH$_2$Cl$_2$ (6 mL) trifluoroacetic acid (TFA, 2 mL) was added. After stirring at room temperature for 16 hours, TFA was removed by passing a stream of compressed air and co-evaporation with acetonitrile. The concentrated residue was subjected to flash column chromatography (silica gel; MeOH/CH$_2$Cl$_2$, 0:10 to 2:8) to afford a mixture of diastereomers (108 mg, 49%). $^1$H NMR (400 MHz, CD$_3$OD) δ 7.14 (d, J=6.8 Hz, 4H), 6.98 (d, J=8.3 Hz, 2H), 6.86-6.77 (m, 9H), 6.70-6.64 (m, 4H), 6.59 (dd, J=8.5, 2.7 Hz, 1H), 6.54 (d, J=8.3 Hz, 3H), 6.33 (d, J=8.4 Hz, 3H), 4.25 (d, J=5.6 Hz, 1H), 4.06-3.97 (m, 4H), 3.96-3.89 (m, 4H), 3.80 (s, 3H), 3.76 (s, 3H), 3.12-2.97 (m, 8H), 1.92-1.87 (m, 6H), 1.85-1.79 (m, 7H). Exchangeable protons (NH$_2$) not observed.

(trans)-N-(4-(4-(6-Methoxy-2-phenyl-1,2,3,4-tetrahydronaphthalen-1-yl)phenoxy)butyl)-4-(trifluoromethyl)cyclohexanecarboxamide. The title compound was synthesized by reaction of 4-(4-(6-methoxy-2-phenyl-1,2,3,4-tetrahydronaphthalen-1-yl)phenoxy)butan-1-amine with (trans)-2,5-dioxopyrrolidin-1-yl-4-(trifluoromethyl)cyclohexane-1-carboxylate in an analogous procedure to the one described for example 1. $^1$H NMR (400 MHz, CD$_3$OD) δ 7.13-7.06 (m, 4H), 6.92 (d, J=8.1 Hz, 2H), 6.80-6.71 (m, 8H), 6.68-6.57 (m, 4H), 6.55 (d, J=10.4 Hz, 1H), 6.46 (d, J=8.1 Hz, 3H), 6.27 (d, J=8.0 Hz, 3H), 4.19 (d, J=5.1 Hz, 1H), 3.92 (t, J=6.0 Hz, 4H), 3.80 (t, J=5.9 Hz, 3H), 3.75 (s, 3H), 3.71 (s, 3H), 3.26-3.16 (m, 5H), 3.09-2.95 (m, 3H), 2.86-2.73 (m, 2H), 2.21-2.04 (m, 8H), 1.98-1.92 (m, 6H), 1.91-1.83 (m, 6H), 1.78-1.69 (m, 6H), 1.69-1.57 (m, 9H), 1.54-1.42 (m, 6H), 1.38-1.27 (m, 6H). Exchangeable proton (NH) not observed.

(trans)-N-(4-(4-(6-Hydroxy-2-phenyl-1,2,3,4-tetrahydronaphthalen-1-yl)phenoxy)butyl)-4-(trifluoromethyl)cyclohexanecarboxamide. A solution of (1r,4r)-N-(4-(4-(6-methoxy-2-phenyl-1,2,3,4-tetrahydronaphthalen-1-yl)phenoxy)butyl)-4-(trifluoromethyl) cyclohexanecarboxamide (84 mg, 0.15 mmol) in CH$_2$Cl$_2$ (2 mL) was cooled to −60° C. BBr$_3$ (290 μL, 1M in CH$_2$Cl$_2$, 2 eq.) was added dropwise and the solution was stirred at −40° C. for 1 h. The reaction was quenched with water (10 mL) and extracted with EtOAc (3×20 mL). The combined organic fractions were washed with brine (20 mL), dried over Na$_2$SO$_4$ and purified by column chromatography (silica gel, EtOAc/Hex, 1:4 to 3:2) to afford the final product as a colorless oil (2 mg, 4%, mixture of diastereomers). $^1$H NMR (400 MHz, CDCl$_3$) δ 7.17-7.14 (m, 4H), 6.99 (d, J=10.1 Hz, 2H), 6.82-6.78 (m, 6H), 6.72-6.68 (m, 2H), 6.61-6.57 (m, 2H), 6.55-6.48 (m, 4H), 6.31 (d, J=8.4 Hz, 3H), 5.56 (br s, 2H, OH), 4.22 (d, J=5.6 Hz, 1H), 3.96 (t, J=6.2 Hz, 3H), 3.85 (t, 3H), 3.38-3.27 (m, 6H), 3.09-2.98 (m, 3H), 2.87-2.72 (m, 1H), 2.03-1.92 (m, 13H), 1.84-1.77 (m, 4H), 1.76-1.70 (m, 4H), 1.69-1.62 (m, 4H), 1.53-1.45 (m, 5H), 1.35-1.27 (m, 4H). Exchangeable proton (OH) not observed.

Example 23. N-(4-(4-(Cyclohexylidene(4-hydroxyphenyl)methyl)phenoxy)butyl)-cyclohexanecarboxamide

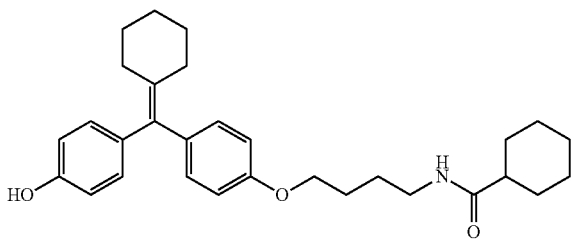 [SMILES: O=C(NCCCCOc1ccc(C(=C2CCCCC2)c2ccc(O)cc2)cc1)C1CCCCC1]

Example 23

The title compound was synthesized by reaction of 4-((4-(4-aminobutoxy)phenyl)(cyclohexylidene)methyl)phenol with 2,5-dioxopyrrolidin-1-yl cyclohexanecarboxylate in an analogous procedure to the one described for example 1. $^1$H NMR (400 MHz, CDCl$_3$) δ 6.97 (dd, J=23.2, 7.3 Hz, 4H), 6.76 (d, J=7.2 Hz, 4H), 6.67 (br s, 1H, OH), 5.71 (br s, 1H, NH), 3.92 (t, J=5.3 Hz, 2H), 3.31 (q, J=5.7 Hz, 2H), 2.26-2.19 (m, 3H), 2.08-1.99 (m, 1H), 1.86-1.72 (m, 7H), 1.70-1.61 (m, 3H), 1.60-1.52 (m, 5H), 1.46-1.35 (m, 2H), 1.29-1.14 (m, 4H). $^{13}$C NMR (100 MHz, CDCl$_3$) δ 176.7, 157.1, 154.7, 138.2, 136.3, 135.5, 133.7, 131.0, 130.3, 129.0, 114.9, 113.8, 67.4, 45.8, 39.2, 32.6, 29.9, 28.8, 27.0, 26.8, 26.6, 25.8.

Example 24. N-(4-(4-(Cyclohexylidene(4-hydroxyphenyl)methyl)phenoxy)-butyl)cyclobutanecarboxamide

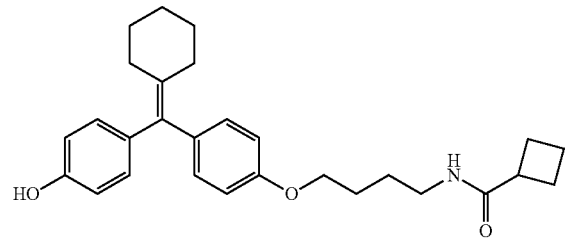 [SMILES: O=C(NCCCCOc1ccc(C(=C2CCCCC2)c2ccc(O)cc2)cc1)C1CCC1]

Example 24

The title compound was synthesized by reaction of 4-((4-(4-aminobutoxy)phenyl)(cyclohexylidene)methyl)phenol with 2,5-dioxopyrrolidin-1-yl cyclobutanecarboxylate in an analogous procedure to the one described for example 1. $^1$H NMR (400 MHz, CDCl$_3$) δ 7.03-6.90 (m, 4H), 6.80-6.72 (m, 4H), 3.92 (t, J=6.0 Hz, 2H), 3.31 (q, J=6.8 Hz, 2H), 3.01-2.91 (m, 1H), 2.27-2.18 (m, 5H), 2.15-2.07 (m, 2H), 1.96-1.88 (m, 1H), 1.86-1.80 (m, 1H), 1.79-1.73 (m, 2H), 1.69-1.63 (m, 2H), 1.60-1.52 (m, 6H). Exchangeable protons (OH, NH) not observed. $^{13}$C NMR (100 MHz, CDCl$_3$) δ 175.6, 157.1, 154.8, 140.6, 138.2, 136.3, 135.4, 133.7, 131.0, 130.3, 129.0, 124.9, 115.2, 114.9, 114.1, 113.8, 67.4, 40.1, 39.3, 32.6, 28.8, 27.0, 26.7, 26.5, 25.5, 18.2.

Example 25. (trans)-N-(4-(4-(Cyclohexylidene(4-hydroxyphenyl)methyl)phenoxy)butyl)-4-(trifluoromethyl)cyclohexanecarboxamide

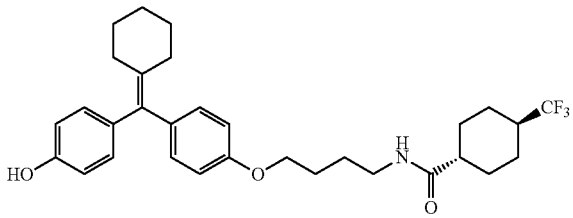 [SMILES: O=C(NCCCCOc1ccc(C(=C2CCCCC2)c2ccc(O)cc2)cc1)[C@H]1CC[C@H](C(F)(F)F)CC1]

Example 25

The title compound was synthesized by reaction of 4-((4-(4-aminobutoxy)phenyl)(cyclohexylidene)methyl)phenol with (trans)-2,5-dioxopyrrolidin-1-yl-4-(trifluoromethyl)cyclohexane-1-carboxylate in an analogous procedure to the one described for example 1. $^1$H NMR (400 MHz, CDCl$_3$) δ 7.04-6.91 (m, 4H), 6.80-6.73 (m, 4H), 5.78 (t, J=5.7 Hz, 1H, NH), 3.92 (t, J=5.9 Hz, 2H), 3.31 (q, J=6.6 Hz, 2H), 2.27-2.19 (m, 3H), 2.06-1.89 (m, 7H), 1.80-1.74 (m, 2H), 1.72-1.65 (m, 2H), 1.61-1.46 (m, 8H), 1.35-1.25 (m, 2H). Exchangeable proton (OH) not observed.

Example 26. N-(4-(4-(Cyclohexylidene(4-hydroxyphenyl)methyl)phenoxy)-butyl)adamantane-1-carboxamide

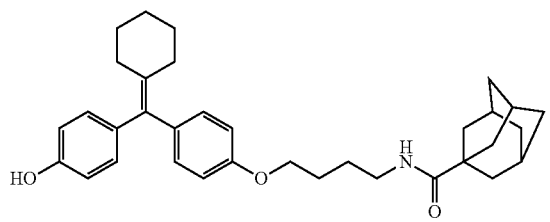 [SMILES: O=C(NCCCCOc1ccc(C(=C2CCCCC2)c2ccc(O)cc2)cc1)C12CC3CC(CC(C3)C1)C2]

Example 26

The title compound was synthesized by reaction of 4-((4-(4-aminobutoxy)phenyl)(cyclohexylidene)methyl)phenol (1S,3s)-2,5-dioxopyrrolidin-1-yl adamantane-1-carboxylate in an analogous procedure to the one described for example 1. $^1$H NMR (400 MHz, CDCl$_3$) δ 7.02-6.92 (m, 4H), 6.79-6.72 (m, 4H), 6.07 (br s, 1H, OH), 5.78 (br s, 1H, NH), 3.93 (t, J=6.0 Hz, 2H), 3.31 (q, J=6.5 Hz, 2H), 2.26-2.19 (m, 2H), 2.09-2.07 (m, 2H), 2.04-1.98 (m, 3H), 1.85-1.80 (m, 5H), 1.78-1.73 (m, 4H), 1.72-1.65 (m, 9H), 1.60-1.53 (m, 4H).

Example 27. 2-((2-(2,6-Dioxopiperidin-3-yl)-1,3-dioxoisoindolin-4-yl)oxy)-N-(4-(4-((6-hydroxy-2-(4-hydroxyphenyl)benzo[b]thiophen-3-yl)oxy)phenoxy)butyl)acetamide

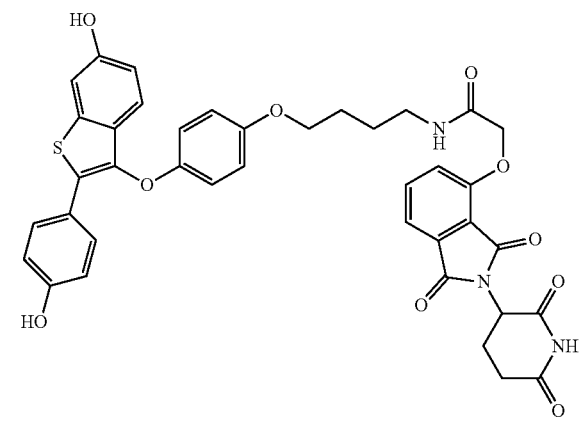 [SMILES: O=C(COc1cccc2c1C(=O)N(C1CCC(=O)NC1=O)C2=O)NCCCCOc1ccc(Oc2c(-c3ccc(O)cc3)sc3cc(O)ccc23)cc1]

Example 27

The title compound was synthesized by reaction of 3-(4-(4-aminobutoxy)phenoxy)-2-(4-hydroxyphenyl)benzo[b]thiophen-6-ol with 2,5-dioxopyrrolidin-1-yl 2-((2-(2,6-dioxopiperidin-3-yl)-1,3-dioxoisoindolin-4-yl)oxy)acetate in an analogous procedure to the one described for example 1. $^1$H NMR (400 MHz, CD$_3$CN) δ 7.74 (t, J=7.8 Hz, 1H), 7.56 (d, J=8.2 Hz, 2H), 7.46 (d, J=7.2 Hz, 1H), 7.31 (d, J=8.2 Hz, 2H), 7.25 (s, 1H), 7.17 (d, J=8.7 Hz, 1H), 6.84-6.75 (m, 7H), 4.99-4.92 (m, 1H), 4.63 (s, 2H), 3.89 (t, J=6.2 Hz, 2H), 3.31 (q, J=6.7 Hz, 2H), 2.72-2.62 (m, 2H), 2.10-2.05 (m, 2H), 1.77-1.69 (m, 2H), 1.67-1.61 (m, 2H). Exchangeable protons (2×OH, NH) not observed. $^{13}$C NMR (100 MHz, CD$_3$CN) δ 172.9, 170.2, 168.0, 167.9, 166.7, 159.8, 156.2, 155.8, 155.3, 153.4, 140.1, 138.0, 137.6, 134.5, 131.2, 128.4, 126.9, 125.4, 123.7, 121.9, 117.5, 117.2, 116.6, 116.4, 114.8, 110.0, 69.2, 68.8, 49.8, 36.0, 32.0, 27.3, 26.7, 23.1, 22.5.

Example 28. N-(4-(4-((6-Hydroxy-2-(4-hydroxyphenyl)benzo[b]thiophen-3-yl)oxy)phenoxy)butyl)cyclobutanecarboxamide

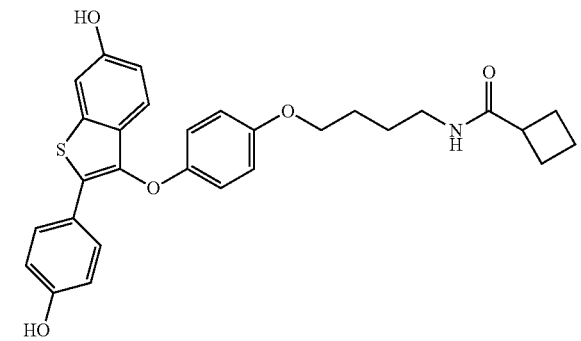 [SMILES: O=C(NCCCCOc1ccc(Oc2c(-c3ccc(O)cc3)sc3cc(O)ccc23)cc1)C1CCC1]

Example 28

The title compound was synthesized by reaction of 3-(4-(4-aminobutoxy)phenoxy)-2-(4-hydroxyphenyl)benzo[b]thiophen-6-ol with 2,5-dioxopyrrolidin-1-yl cyclobutanecarboxylate in an analogous procedure to the one described for example 1. $^1$H NMR (400 MHz, CD$_3$OD) δ 7.54 (d, J=6.6 Hz, 2H), 7.18-7.12 (m, 2H), 6.84-6.74 (m, 7H), 3.90 (t, J=6.1 Hz, 2H), 3.21 (t, J=6.8 Hz, 2H), 3.10-3.01 (m, 1H), 2.25-2.16 (m, 2H), 2.13-2.04 (m, 2H), 2.02-1.91 (m, 1H), 1.86-1.78 (m, 1H), 1.76-1.69 (m, 1H), 1.67-1.60 (m, 2H). Exchangeable protons (2×OH, NH) not observed.

Example 29. 3,3-Difluoro-N-(4-(4-((6-hydroxy-2-(4-hydroxyphenyl)benzo[b]thiophen-3-yl)oxy)phenoxy)butyl)cyclobutanecarboxamide

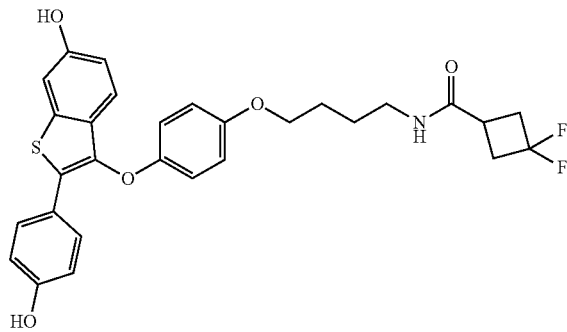 [SMILES: O=C(NCCCCOc1ccc(Oc2c(-c3ccc(O)cc3)sc3cc(O)ccc23)cc1)C1CC(F)(F)C1]

Example 29

The title compound was synthesized by reaction of 3-(4-(4-aminobutoxy)phenoxy)-2-(4-hydroxyphenyl)benzo[b]thiophen-6-ol with 2,5-dioxopyrrolidin-1-yl 3,3-difluorocyclobutanecarboxylate in an analogous procedure to the one described for example 1. $^1$H NMR (400 MHz, CD$_3$CN) δ 7.53 (d, J=8.7 Hz, 2H), 7.16-7.11 (m, 2H), 6.83-6.72 (m, 7H), 3.89 (t, J=6.1 Hz, 2H), 3.22 (t, J=6.8 Hz, 2H), 2.88-2.79 (m, 1H), 2.78-2.61 (m, 4H), 1.75-1.69 (m, 2H), 1.67-1.60 (m, 2H).

Example 30. 3-Cyclohexyl-N-(4-(4-((6-hydroxy-2-(4-hydroxyphenyl)benzo[b]thiophen-3-yl)oxy)phenoxy)butyl)propanamide

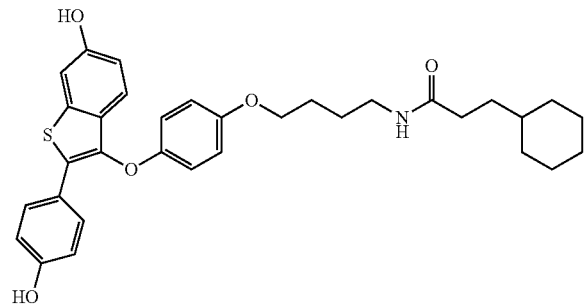 [SMILES: O=C(CCC1CCCCC1)NCCCCOc1ccc(Oc2c(-c3ccc(O)cc3)sc3cc(O)ccc23)cc1]

Example 30

The title compound was synthesized by reaction of 3-(4-(4-aminobutoxy)phenoxy)-2-(4-hydroxyphenyl)benzo[b]thiophen-6-ol with 2,5-dioxopyrrolidin-1-yl 3-cyclohexylpropanoate in an analogous procedure to the one described for example 1. $^1$H NMR (400 MHz, CD$_3$OD) δ 7.53 (d, J=8.2 Hz, 2H), 7.17-7.10 (m, 2H), 6.83-6.73 (m, 7H), 3.90 (t, J=6.2 Hz, 2H), 3.20 (t, J=6.7 Hz, 2H), 2.17 (t, J=7.9 Hz, 2H), 1.77-1.69 (m, 4H), 1.67-1.61 (m, 3H), 1.51-1.42 (m, 3H), 1.32-1.15 (m, 5H), 0.96-0.85 (m, 2H). Exchangeable protons (2×OH, NH) not observed. $^{13}$C NMR (100 MHz, CD$_3$OD) δ 176.6, 158.3, 156.8, 155.6, 153.1, 139.8, 137.5, 131.5, 128.6, 126.7, 125.7, 123.7, 117.2, 116.6, 116.1, 115.4, 108.1, 68.7, 40.0, 38.6, 34.7, 34.6, 33.8, 28.1, 27.6, 27.4, 27.0.

Example 31. N-(4-(4-(Adamantan-2-ylidene(4-hydroxyphenyl)methyl)phenoxy)butyl)cyclopropanecarboxamide

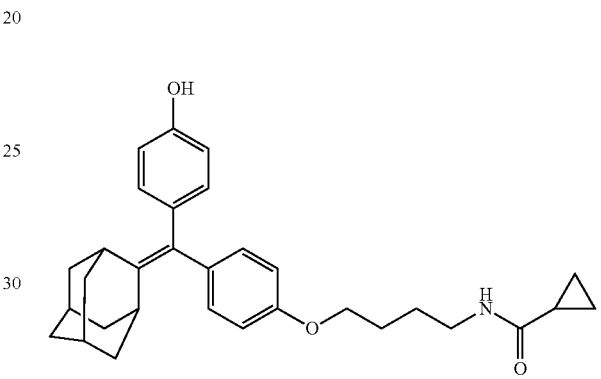

Example 31

The title compound was synthesized by reaction of 4-(adamantan-2-ylidene(4-(4-aminobutoxy)phenyl)methyl)phenol with 2,5-dioxopyrrolidin-1-yl cyclopropanecarboxylate in an analogous procedure to the one described for example 1. White foam; $^1$H NMR (400 MHz, CDCl$_3$) δ 7.03-6.95 (m, 4H), 6.80-6.71 (m, 4H), 5.73 (br s, 1H, OH), 3.95 (t, J=6.1 Hz, 2H), 3.34 (q, J=6.0, 5.6 Hz, 2H), 2.77 (br s, 2H), 2.01-1.96 (m, 2H), 1.88-1.79 (m, 12H), 1.73-1.67 (m, 2H), 1.31-1.24 (m, 1H), 0.98-0.94 (m, 2H), 0.71 (dd, J=7.8, 3.2 Hz, 2H). Exchangeable proton (NH) not observed.

Example 32. N-(4-(4-(Adamantan-2-ylidene(4-hydroxyphenyl)methyl)phenoxy)butyl)-2,2-difluorocyclopropanecarboxamide

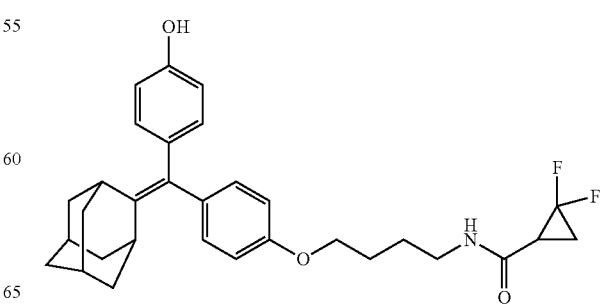

Example 32

The title compound was synthesized by reaction of 4-(adamantan-2-ylidene(4-(4-aminobutoxy)phenyl)methyl)phenol with 2,5-dioxopyrrolidin-1-yl 2,2-difluorocyclopropanecarboxylate in an analogous procedure to the one described for example 1. Yellow oil; $^1$H NMR (400 MHz, CDCl$_3$) δ 7.03-6.93 (m, 4H), 6.80-6.71 (m, 4H), 5.97 (br s, 1H, OH), 5.80 (br s, 1H, NH), 3.97-3.92 (m, 2H), 3.39-3.32 (m, 2H), 2.80-2.73 (m, 2H), 2.25-2.19 (m, 1H), 2.11-2.03 (m, 2H), 2.01-1.97 (m, 2H), 1.87-1.81 (m, 12H), 1.74-1.69 (m, 2H).

Example 33. N-(4-(4-(Adamantan-2-ylidene(4-hydroxyphenyl)methyl)phenoxy)butyl)-4-(trifluoromethyl)benzamide

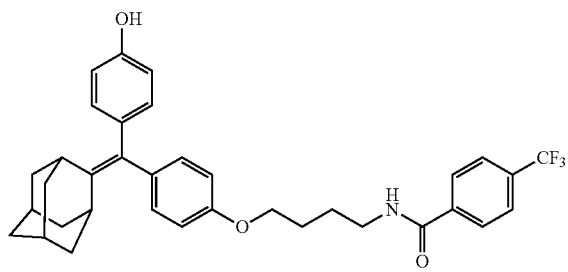 [SMILES: O=C(NCCCCOc1ccc(C(=C2C3CC4CC(C3)CC2C4)c2ccc(O)cc2)cc1)c1ccc(C(F)(F)F)cc1]

Example 33

The title compound was synthesized by reaction of 4-(adamantan-2-ylidene(4-(4-aminobutoxy)phenyl)methyl)phenol with 2,5-dioxopyrrolidin-1-yl 4-(trifluoromethyl)benzoate in an analogous procedure to the one described for example 1. White solid; $^1$H NMR (400 MHz, CDCl$_3$) δ 7.85 (d, J=7.8 Hz, 2H), 7.64 (d, J=7.9 Hz, 2H), 6.98 (dd, J=26.3, 8.0 Hz, 4H), 6.81-6.73 (m, 4H), 3.97 (t, J=5.3 Hz, 2H), 3.56-3.50 (m, 2H), 2.77 (d, J=9.9 Hz, 2H), 2.02-1.95 (m, 2H), 1.88-1.79 (m, 14H). Exchangeable protons (OH, NH) not observed.

Example 34. N-(4-(4-(Adamantan-2-ylidene(4-hydroxyphenyl)methyl)phenoxy)butyl)-3-cyclohexylpropanamide

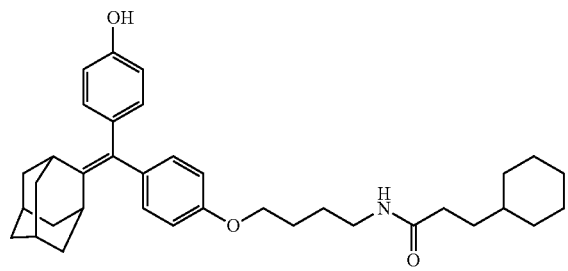 [SMILES: O=C(CCC1CCCCC1)NCCCCOc1ccc(C(=C2C3CC4CC(C3)CC2C4)c2ccc(O)cc2)cc1]

Example 34

The title compound was synthesized by reaction of 4-(adamantan-2-ylidene(4-(4-aminobutoxy)phenyl)methyl)phenol with 2,5-dioxopyrrolidin-1-yl 3-cyclohexylpropanoate in an analogous procedure to the one described for example 1. Pale yellow solid; $^1$H NMR (400 MHz, CDCl$_3$) δ 7.03-6.91 (m, 4H), 6.79-6.73 (m, 4H), 5.70 (br s, 1H, OH), 3.93 (t, J=6.0 Hz, 2H), 3.31 (q, J=6.6 Hz, 2H), 2.77 (d, J=11.9 Hz, 2H), 2.19-2.13 (m, 2H), 1.97 (br s, 2H), 1.86-1.77 (m, 10H), 1.70-1.63 (m, 6H), 1.59-1.55 (m, 2H), 1.50 (q, J=7.3 Hz, 3H), 1.19 (dd, J=20.5, 8.8 Hz, 6H). Exchangeable proton (NH) not observed.

Biological Assays

Tritiated estradiol was obtained from Perkin Elmer and purified, full-length human estrogen receptor a from Invitrogen.

Competitive radiometric binding assays (RBA) were performed on 96-well microtiter filter plates (Millipore), using full length human estrogen receptor a, with tritiated estradiol as tracer, as previously described (Carlson K E, Choi I, Gee A, Katzenellenbogen B S, Katzenellenbogen J A. Altered ligand binding properties and enhanced stability of a constitutively active estrogen receptor: evidence that an open pocket conformation is required for ligand interaction. Biochemistry 1997, 36(48), 14897-14905). After incubation on ice for 18-24 h, ERα-bound tracer was absorbed onto hydroxyapatite (BioRad), washed with buffer, and measured by scintillation counting. RBA values are the average SD of 2-3 determinations.

Cell proliferation assay: WST-1 assay (Roche, Basel, Switzerland) was used to quantify cell viability after a 6-day exposure to compounds, as described in Gong et al. *Mol. Cell. Endocrinol.* 2016, 437, 190-200. Absorbance was measured at 450 nm using a VICTOR X5 PerkinElmer 2030 Multilabel Plate Reader, and cell proliferation values represent signal from compound-treated samples relative to vehicle-treated controls. All assays were performed in triplicate, and the values shown are the average SD of 2-3 independent experiments.

In-cell western assay: Cells were cultured in 96-well plates at 3000 cells/well, and treated with compound for 24 h. Cells were washed twice in PBS, fixed with 4% formaldehyde (Fisher Scientific) solution in PBS, permeabilized in 0.1% Triton X-100 in PBS, blocked with Odyssey Blocking Buffer (LI-COR), and incubated with rabbit HC-20 ERα antibody (Santa Cruz, Cat #SC-543) at 4° C. overnight. Both IRDye 800 CW goat anti-rabbit secondary antibody (LI-COR, Cat #926-32211) and Cell Tag 700 (LI-COR, Cat #926-41090) were diluted (1:600) for incubation with cells. Plates were washed and ERα staining signals were quantified and normalized with Cell Tag signals using LI-COR Odyssey infrared imaging system. The ERα protein levels were calculated relative to the vehicle-treated samples. All assays were performed in triplicate.

TABLE 1

| Example # | RBA (estradiol = 100) | Antiproliferation IC$_{50}$ (nM) | ERα Downregulation IC$_{50}$ (nM) |
|---|---|---|---|
| 1 | 20 ± 6 | 16 | 0.5 |
| 2 | 14 ± 1 | 36 | 636 |
| 3 | 14 ± 4 | 7 | 307 |
| 4 | 21 ± 6 | 17 | ND |
| 5 | 26 ± 6 | 9 | 3 |
| 6 | 11 ± 3 | 13 | 6 |
| 7 | 6.0 ± 0.1 | 5 | 10 |
| 8 | 17 ± 2 | 12 | 2 |

TABLE 1-continued

| Example # | RBA (estradiol = 100) | Antiproliferation IC$_{50}$ (nM) | ERα Downregulation IC$_{50}$ (nM) |
|---|---|---|---|
| 9 | 37 ± 0.3 | 9 | 0.5 |
| 10 | 70 ± 1 | 3 | ND |
| 11 | 28 ± 6 | 0.6 | 0.4 |
| 12 | 30 ± 5 | 5 | ND |
| 13 | 30 ± 0.1 | 4 | ND |
| 14 | 10 ± 0.4 | 0.5 | 2 |

ND = not determined

Luciferase assays were performed to determine the efficacy of the example compounds at inhibiting ER or its mutants' ability to activate transcription of genes.

Cells were plated at a density of 0.15×10$^6$ per well of 24 well plates one day prior to transfection. Cells were transfected with 125 ng (per well) of HA-ERα wild type or mutants, 315 ng (per well) of 3×-ERE-TATA-Luciferase reporter and 50 ng (per well) of pRL-TK Renilla Luciferase plasmid, using Xtremegene (Roche). The cells were treated with the various compounds or Fulvestrant at the indicated doses a day after transfection for 24 hours and luciferase activities were determined using the Dual-Luciferase® Reporter Assay System (Promega) according to manufacturer's instructions. Luciferase bioluminescence measurements were performed with the Veritas™ Microplate Luminometer (Promega). All experiments were conducted in triplicate and the Firefly luciferase activity was normalized with the Renilla luciferase activity of each sample. Data is shown in Tables 2, 3, and 4.

TABLE 2

| Ex. # | Overexpressed ER (% Inhibition)$^a$ | | | |
|---|---|---|---|---|
| | WT | L536R | Y537S | D538G |
| 1 | 71 | 70 | 62 | 84 |
| 6 | 84 | 70 | 62 | 87 |
| 7 | 83 | 77 | 46 | 83 |
| 8 | 83 | 84 | 31 | 89 |
| 9 | 88 | 89 | 33 | 92 |
| 10 | 84 | 78 | 11 | 89 |
| 11 | 89 | 79 | 86 | 91 |
| 12 | 90 | 87 | 58 | 92 |
| 13 | 90 | 90 | 46 | 92 |
| 14 | 81 | 82 | 26 | 88 |
| 15 | 85 | 82 | −51 | 93 |
| 16 | 81 | 64 | −65 | 61 |
| 17 | 96 | 94 | 95 | 95 |
| 18 | 80 | 84 | −75 | 86 |
| 19 | 82 | 83 | −136 | 90 |
| 20 | 83 | ND | ND | ND |
| 21 | 82 | ND | ND | ND |
| 22 | −130 | ND | ND | ND |
| 23 | −25 | 43 | −169 | 0 |
| 24 | −83 | −75 | −160 | −7 |
| 25 | 77 | 36 | −39 | 42 |
| 26 | 52 | 69 | −32 | 65 |
| 28 | 13 | 43 | −64 | 60 |
| 29 | 39 | 90 | 1 | 73 |
| 30 | 61 | ND | ND | ND |
| 31 | 36 | ND | ND | ND |
| 32 | 48 | ND | ND | ND |
| 33 | 79 | ND | ND | ND |
| 34 | 65 | ND | ND | ND |

$^a$Compound concentration: 1 μM.
ND = not determined.

TABLE 3

| | | CRISPR KI (% Inhibition) | | | |
|---|---|---|---|---|---|
| | MCF7 (% | Y537S | | D538G | |
| Ex. # | Inhibition) | cl. 4 | cl. 24 | cl. 50 | cl. 65 |
| 1 | 71 | −74 | −34 | 15 | 71 |
| 6 | 70 | −187 | −108 | 68 | 73 |
| 7 | 53 | −70 | −64 | 15 | 44 |
| 8 | 77 | −387 | −249 | 39 | 78 |
| 9 | 73 | −369 | −384 | 34 | 72 |
| 10 | 66 | −580 | −496 | 19 | 65 |
| 11 | 84 | −62 | −10 | 74 | 84 |
| 12 | 82 | −232 | −199 | 36 | 80 |
| 13 | 80 | −334 | −327 | 32 | 77 |
| 14 | 72 | −342 | −421 | 67 | 73 |

TABLE 4

| | IC$_{90}$ (nM) | | | |
|---|---|---|---|---|
| Example # | WT | L536R | Y537S | D538G |
| 17 | 18.97 | 124.4 | 463.9 | 174.6 |

Cell proliferation assays were performed to determine the efficacy of the compounds at inhibiting ER or its mutants' ability at promoting cell proliferation.

Cells were plated at 1500 cells/well into 96-well culture plates in regular media, treated with the indicated doses of the compounds or Fulvestrant the next day and incubated in a humidified incubator with 5% CO$_2$ at 37° C. They were assayed for cell proliferation at Day 0, 3, 5 and 7 using the Resazurin reagent (R&D Systems), which upon addition, culture plates were incubated at 37° C. incubator for 4 hours before their fluorescence were read at 560 nm excitation and 590 nm emission wavelengths with a microtiter plate reader (Molecular Devices). Data shown in Table 5.

TABLE 5

| | IC$_{90}$ (nM) | | |
|---|---|---|---|
| Example # | MCF7 | Y537S cl. 24 | D538G cl. 65 |
| 17 | 22.11 | 303.7 | 315.1 |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A compound of formula (I):

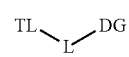

wherein:
TL is chosen from:

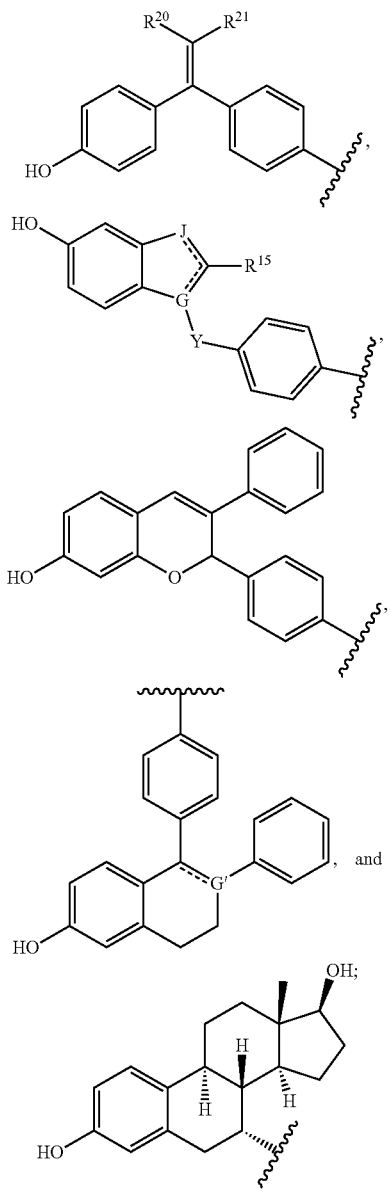

, and

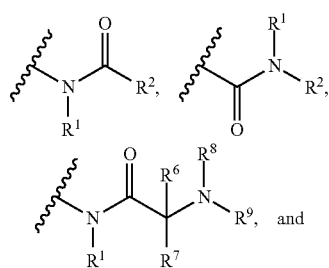

L is selected from divalent $(C_3-C_7)$hydrocarbyl, $(C_2-C_{10})$oxaalkyl, and $(C_2-C_{10})$azaalkyl;
DG is selected from:

-continued

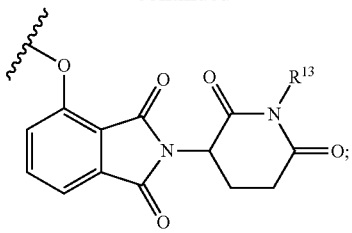

$R^{20}$ and $R^{21}$ are independently a $(C_1-C_{12})$hydrocarbyl, or, taken together along with the carbon to which they are attached, $R^{20}$ and $R^{21}$ optionally combine to form a $(C_3-C_{12})$carbocyclyl;
substructure

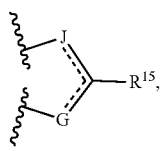

as drawn above, represents either

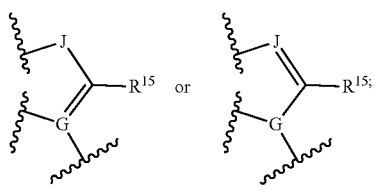

wherein:
J is selected from: S, O, and $NR^{17}$, and, G is C when

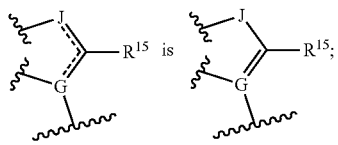

and
J is C—$R^{16}$ and G is N when

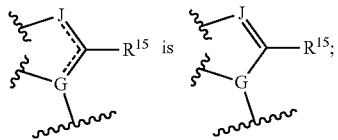

Y is —O— or —$CH_2$—;

---- G′ represents either a single or a double bond connecting a carbon atom to G';
G' is CH or N when

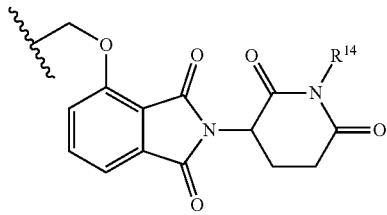

is a single bond, or, G' is C when

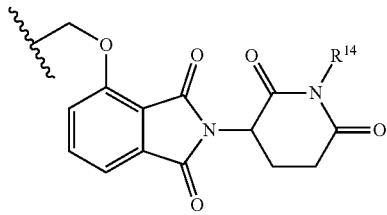

is a double bond;
$R^1$ is selected from H and $(C_1\text{-}C_3)$alkyl;
$R^2$ is

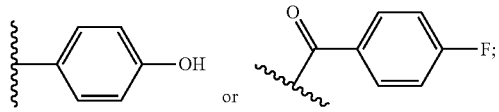 [SMILES: *c1ccc(O)cc1 ; *C(=O)c1ccc(F)cc1]

or optionally substituted $(C_1\text{-}C_{15})$hydrocarbyl, wherein the optional substituents for $(C_1\text{-}C_{15})$hydrocarbyl are selected from halo and $(C_1\text{-}C_3)$perfluoroalkyl;
$R^5$ and $R^6$ are selected from H and $(C_1\text{-}C_3)$alkyl;
$R^7$ is selected from any of the sidechains present in naturally-occurring α-amino acids;
$R^8$ is H or $(C_1\text{-}C_3)$alkyl;
$R^9$ is chosen from H, $(C_1\text{-}C_3)$alkyl, or —C(=O)—O—$(C_1\text{-}C_6)$alkyl;
$R^{13}$ and $R^{14}$ are selected from H and $(C_1\text{-}C_3)$alkyl;
$R^{15}$ is

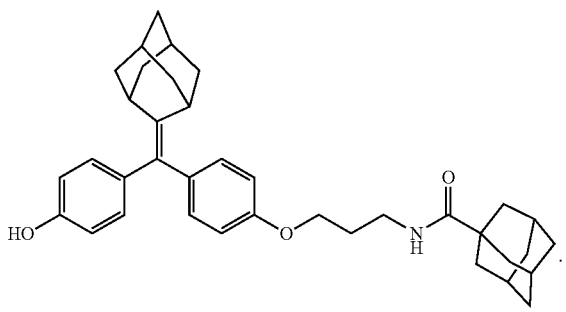 [SMILES: O=C(NCCCOc1ccc(C(=C2C3CC4CC(C3)CC2C4)c2ccc(O)cc2)cc1)C12CC3CC(CC(C3)C1)C2]

and
$R^{16}$ and $R^{17}$ are selected from: H and $(C_1\text{-}C_6)$alkyl;
with the proviso that the compound is not:

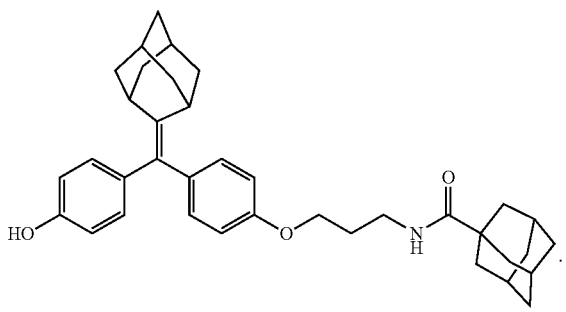 [SMILES: O=C(NCCCOc1ccc(C(=C2C3CC4CC(C3)CC2C4)c2ccc(O)cc2)cc1)C12CC3CC(CC(C3)C1)C2]

2. A compound according to claim 1, wherein the compound of formula (I) is a compound of formula (II):

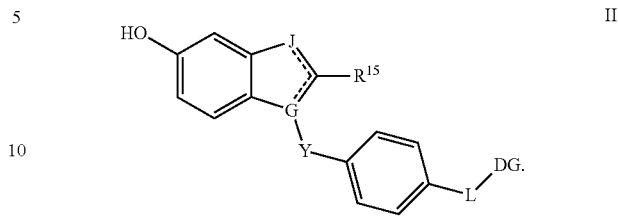

3. A compound according to claim 2, wherein:

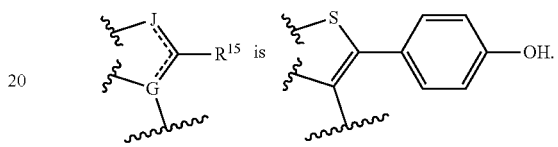

4. A compound according to claim 2, wherein:

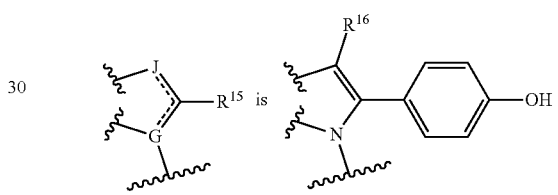

and $R^{16}$ is $(C_1\text{-}C_3)$alkyl.

5. A compound according to claim 3, wherein Y is —O—.

6. A compound according to claim 4, wherein Y is —CH$_2$—.

7. A compound according to claim 4, wherein $R^{16}$ is methyl.

8. A compound according to claim 1, wherein the compound of formula (I) is a compound of formula (III):

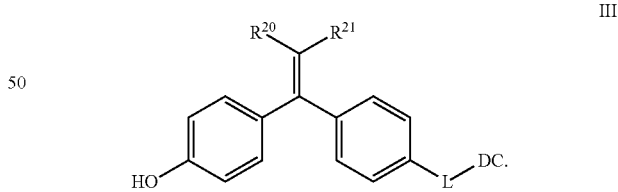

9. A compound according to claim 8, wherein DG is

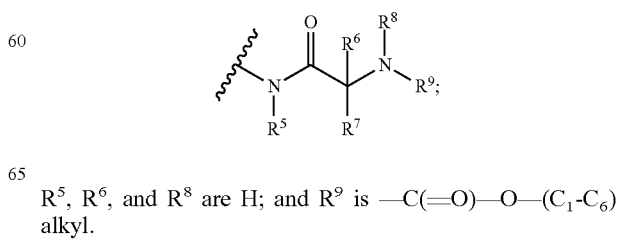

$R^5$, $R^6$, and $R^8$ are H; and $R^9$ is —C(=O)—O—$(C_1\text{-}C_6)$alkyl.

10. A compound according to claim 9, wherein $R^7$ is chosen from

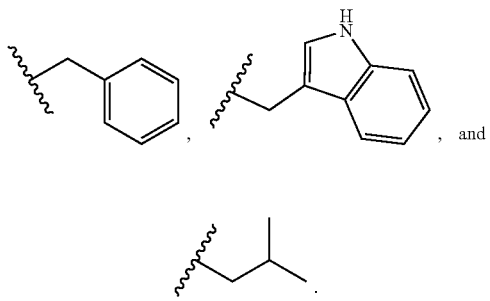, and

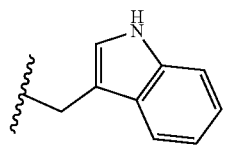.

11. A compound according to claim 10, wherein $R^7$ is

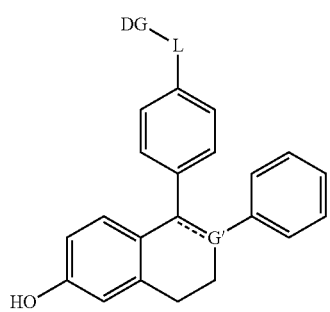.

12. A compound according to claim 1, wherein the compound of formula (I) is a compound of formula (IV):

IV

[structure of formula IV shown with DG-L attached to phenyl, connected to naphthalenyl with HO substituent, bearing phenyl group via G']

13. A compound according to claim 12, wherein

==== G' is a carbon-carbon single bond.

14. A compound according to claim 1, wherein:
DG is

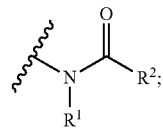;

$R^1$ is hydrogen;
$R^2$ is —(CH$_2$)$_m$R$^{22}$;
$R^{22}$ is optionally substituted (C$_3$-C$_9$)carbocyclyl, wherein the optional substituents for said (C$_3$-C$_9$)carbocyclyl are selected from halo, (C$_1$-C$_3$)alkyl, and (C$_1$-C$_3$)perfluoroalkyl; and
m is 0, 1, 2, or 3.

15. A compound according to claim 14, wherein L is divalent (C$_2$-C$_6$)oxaalkyl.

16. A compound according to claim 15, wherein L is —O(CH$_2$)$_n$— and n is 2, 3, 4, 5, or 6.

17. A compound according to claim 16, wherein n is 4.

18. A compound according to claim 1, wherein DG is

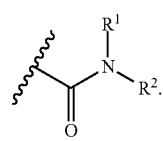.

19. A compound according to claim 18, wherein $R^1$ is hydrogen.

20. A method for treating breast cancer in a patient diagnosed with breast cancer or to a patient reporting one or more physiological symptoms of breast cancer, the method comprising administering to the patient a therapeutically effective amount of the compound according to claim 1.

21. The method according to claim 20, wherein said breast cancer is chemotherapy-resistant breast cancer.

22. A method for restoring sensitivity to one or more chemotherapeutic agents in the treatment of breast cancer in a patient diagnosed with breast cancer or in a patient reporting one or more physiological symptoms of breast cancer, the method comprising administering to the patient a therapeutically effective amount of a compound according to claim 1.

23. A method for destroying ERα receptors by exposing said receptors with a compound that includes a targeting ligand TL tethered via L to a recognition motif or degron DG in a patient comprising administering to the patient a therapeutically effective amount of the compound according to claim 1.

24. A pharmaceutical composition comprising a pharmaceutically acceptable carrier and the compound according to claim 1.

* * * * *